US008951742B2

(12) United States Patent
Wollert et al.

(10) Patent No.: US 8,951,742 B2
(45) Date of Patent: Feb. 10, 2015

(54) ASSESSING SUSCEPTIBILITY TO CARDIAC INTERVENTION, SUSCEPTIBILITY TO THERAPY FOR HEART FAILURE, RISK OF MORTALITY OR FURTHER CARDIOVASCULAR EVENTS, AND RISK OF SUBSEQUENT PULMONARY EMBOLISM IN RELEVANT PATIENTS BASED ON DETERMINATIONS OF GDF-15, NATRIURETIC PEPTIDE, CARDIAC TROPONIN OR COMBINATIONS THEREOF

(75) Inventors: Kai C. Wollert, Hannover (DE); Tibor Kempf, Hannover (DE); Lars Wallentin, Uppsala (SE); Helmut Drexler, Hannover (DE); Christa Marianne Drexler, legal representative, Freiburg im Breisgau (DE); Beatrice Drexler, legal representative, Basel (CH)

(73) Assignee: Medizinische Hochschule Hannover, Hannover (DE)

( * ) Notice: Subject to any disclaimer, the term of this patent is extended or adjusted under 35 U.S.C. 154(b) by 370 days.

(21) Appl. No.: 12/363,932

(22) Filed: Feb. 2, 2009

(65) Prior Publication Data
US 2011/0065204 A1 Mar. 17, 2011

Related U.S. Application Data

(60) Provisional application No. PCT/EP2007/058007, filed on Aug. 2, 2007.

(30) Foreign Application Priority Data

Aug. 4, 2006 (EP) ..................................... 06118464
Sep. 28, 2006 (EP) ..................................... 06121413
May 24, 2007 (EP) ..................................... 07108854

(51) Int. Cl.
*G01N 33/53* (2006.01)
*G01N 33/68* (2006.01)

(52) U.S. Cl.
CPC ...... *G01N 33/6893* (2013.01); *G01N 2333/475* (2013.01); *G01N 2333/58* (2013.01); *G01N 2800/324* (2013.01); *G01N 2800/52* (2013.01); *G01N 2800/325* (2013.01)
USPC ........................................................ 435/7.2

(58) Field of Classification Search
None
See application file for complete search history.

(56) References Cited

U.S. PATENT DOCUMENTS

2003/0004565 A1* 1/2003 Harnek et al. ............... 623/1.15
2003/0013097 A1 1/2003 Welsh et al.
2003/0022235 A1* 1/2003 Dahlen et al. ................. 435/7.1
2003/0152519 A1* 8/2003 Koenig et al. ................ 424/9.41
2003/0232385 A1* 12/2003 Breit et al. .................... 435/7.1
2004/0096919 A1 5/2004 Davey et al.
2004/0215087 A1* 10/2004 Genero et al. ................ 600/508
2004/0215240 A1* 10/2004 Lovett et al. ...................... 607/4

FOREIGN PATENT DOCUMENTS

| EP | 1363128 A2 | | 11/2003 |
| WO | WO 96/24373 | * | 8/1996 |
| WO | 00/70051 A1 | | 11/2000 |
| WO | 01/81928 A1 | | 11/2001 |
| WO | 2005/003764 A3 | | 1/2005 |
| WO | 2005/124364 A1 | | 12/2005 |

OTHER PUBLICATIONS

Kempf, Circulation, 2005, vol. 112, issue 17, Supplement, abstract 1420.*
Kempf, Ciruclation Research, 2006, vol. 98, pp. 351-360.*
International Search Report issued Apr. 17, 2008 in Application No. PCT/EP2007/058007, 7 pages.
Brown, David A. et al., "Concentration in plasma of macrophage inhibitory cytokine-1 and risk of cardiovascular events in women: a nested case-control study," The Lancet, Jun. 22, 2002, pp. 2159-2163, vol. 359.
Giannitsis, Evangelos et al., "Independent Prognostic Value of Cardiac Troponin T in Patients With Confirmed Pulmonary Embolism," Circulation, 2000, pp. 211-217, vol. 102.
Kempf, Tibor et al., "The transforming growth factor-beta superfamily member growth differentiation factor-15 protects the heart from ischemia/reperfusion injury," Circulation Research, Online Data Supplement, Feb. 17, 2006, 6 pages, vol. 98, No. 3.
Kempf, Tibor et al., "Growth-Differentiation Factor-15 is a New Powerful Biomarker in Patients with Chronic Heart Failure," Circulation, 79th Annual Scientific Session of the American Heart Association, Nov. 12-15, 2006, Abstracts From Scientific Sessions, Abstract No. 3389.
Ten Wolde, M. et al., "Brain Natriuretic Peptide as a Predictor of Adverse Outcome in Patients With Pulmonary Embolism," Circulation, 2003, pp. 2082-2084, vol. 107.
Wollert, Kai C. et al., "Prognostic Value of Growth-Differentiation Factor-15 in Patients With Non-ST-Elevation Acute Coronary Syndrome," Circulation, 2007, pp. 962-971, vol. 115.

* cited by examiner

*Primary Examiner* — Michael Pak
(74) *Attorney, Agent, or Firm* — McDonnell Boehnen Hulbert & Berghoff LLP

(57) ABSTRACT

The present invention relates to a method of identifying a subject being susceptible to a cardiac intervention based on the determination of GDF-15 in a sample of a subject in need of a cardiac intervention. Moreover, the present invention pertains to a method for predicting the risk of mortality or a further acute cardiovascular event for a subject suffering from a cardiovascular complication based on the determination of GDF-15 and a natriuretic peptide and/or a cardiac troponin in a sample the said subject. Also encompassed by the present invention are devices and kits for carrying out the aforementioned methods.

35 Claims, 9 Drawing Sheets

ASSESSING SUSCEPTIBILITY TO CARDIAC INTERVENTION, SUSCEPTIBILITY TO THERAPY FOR HEART FAILURE, RISK OF MORTALITY OR FURTHER CARDIOVASCULAR EVENTS, AND RISK OF SUBSEQUENT PULMONARY EMBOLISM IN RELEVANT PATIENTS BASED ON DETERMINATIONS OF GDF-15, NATRIURETIC PEPTIDE, CARDIAC TROPONIN OR COMBINATIONS THEREOF

RELATED APPLICATIONS

This application is a continuation of PCT/EP2007/058007 filed Aug. 2, 2007 and claims priority to EP 07108854.6 filed May 24, 2007, EP 06121413.6 filed Sep. 28, 2006, and EP 06118464.4 filed Aug. 4, 2006.

FIELD OF THE INVENTION

The present invention relates to a method of identifying a subject being susceptible to a cardiac intervention based on the determination of growth differentiation factor-15 (GDF-15) in a sample of a subject in need of a cardiac intervention. Moreover, the present invention pertains to a method for predicting the risk of mortality or an acute cardiovascular event for a subject suffering from a cardiovascular complication based on the determination of GDF-15 and a natriuretic peptide and/or a cardiac troponin in a sample the said subject. Also encompassed by the present invention are devices and kits for carrying out the aforementioned methods.

BACKGROUND OF THE INVENTION

An aim of modern medicine is to provide personalized or individualized treatment regimens. Those are treatment regimens which take into account a patient's individual needs or risks. Personalized or individual treatment regimens shall be also taken into account for emergency measures. Specifically, in the case of acute cardiovascular events, a decision for a certain treatment regimen must be made, usually, within a short period of time. Cardiovascular complications, particularly heart diseases, are the leading cause of morbidity and mortality in the Western hemisphere. Cardiovascular complications can remain asymptomatic for long periods of time. However, they may have severe consequences once an acute cardiovascular event, such as myocardial infarction, as a cause of the cardiovascular complication occurs.

The conventional diagnostic techniques for cardiovascular complications include electrocardiographic and echocardiographic measurements, analysis of symptoms and previous medical history of the patient, such as chest pain, and analysis of some clinical parameters. Recently, these conventional techniques have been further strengthened by the analysis of biomarkers and, in particular, by the analysis of the levels for cardiac troponins in blood samples of emergency patients. Moreover, natriuretic peptides are also described as suitable biomarkers for diagnosing cardiovascular complications. Even more recently, GDF-15 has been suggested to be an indicator for cardiovascular complications, too (US2003/0232385; Kempf 2006, Circ Res 98: 351-360). Growth differentiation factor-15 (GDF-15) is a member of the transforming growth factor-β cytokine superfamily. GDF-15 was first identified as macrophage-inhibitory cytokine-1 (MIC-1), and later also named placental transforming growth factor-β (Bootcov 1997, Proc Natl Acad Sci 94:11514-11519; Tan 2000, Proc Natl Acad Sci 97:109-114). It has recently been shown that cultured cardiomyocytes express and secrete GDF-15 via nitric oxide and nitrosative stress-dependent signaling pathways when subjected to simulated ischemia and reperfusion. Moreover, it has been observed in a mouse model of myocardial ischemia and reperfusion injury that GDF-15 expression levels rapidly increase in the ischemic area following coronary artery ligation, and remain elevated in the reperfused myocardium for several days (Kempf loc. cit).

The conventional diagnostic techniques, specifically for emergency situations, usually do not allow for a reliable diagnosis and/or risk assessment. Thus, based on said diagnostic techniques, a personalized treatment regimen can not be determined with sufficient accuracy. As a consequence thereof, many patients will receive a treatment regimen which is insufficient or which may have adverse side effects. In many cases, acute cardiovascular events, once determined by the conventional diagnostic techniques referred to above and/or by troponin levels of the patient, are currently treated by cardiac interventions. Those cardiac interventions include various types of angioplasty-based interventions and/or coronary bypass surgery which are carried out in order to restore proper blood flow, e.g., within the coronary vessels. However, those interventions are not always successful and may be even harmful for the patient. In addition, the interventions are time and cost expensive. The same difficulties and deficiencies of current risk assessment techniques arise for interventions in patients with heart failure, e.g., drug therapies, such as treatment with an angiotensin converting enzyme inhibitor, angiotensin receptor blocker, beta-blocker, or aldosterone-antagonist, and interventional therapies, such as cardiac resynchronisation therapy (CRT) or the implantable cardioverter-defibrillator (ICD).

Therefore, there is a need for diagnostic or prognostic measures which allow an individual risk stratification for a patient who is suspected to be in need for a certain treatment regimen such as a cardiac intervention. Furthermore, there is a need for a reliable general risk stratification including the risk for mortality or recurrent adverse cardiovascular events in patients suffering from a cardiovascular complication and, especially, in patients exhibiting an acute cardiovascular event or heart failure.

The technical problem underlying the present invention can be seen as the provision of means and methods for complying with the aforementioned needs.

The technical problem is solved by the embodiments characterized in the claims and herein below.

SUMMARY OF THE INVENTION

Accordingly, the present invention relates to a method of identifying a subject being susceptible to a cardiac intervention comprising
 (a) determining the amount of GDF-15 in a sample of a subject in need of a cardiac intervention; and
 (b) comparing the amount of GDF-15 determined in step a) to a reference amount, whereby a subject susceptible to a cardiac intervention is to be identified.

The method of the present invention, preferably, is an in vitro method. Moreover, it may comprise steps in addition to those explicitly mentioned above. For example, further steps may relate to sample pre-treatments or evaluation of the results obtained by the method. The method of the present invention may be also used for monitoring, confirmation, and subclassification of a subject in need of a cardiac intervention. The method may be carried out manually or assisted by automation. Preferably, step (a) and/or (b) may in total or in part be assisted by automation, e.g., by a suitable robotic and sensory equipment for the determination in step (a) or a computer-implemented comparison in step (b).

DETAILED DESCRIPTION OF THE INVENTION

Figure 1:
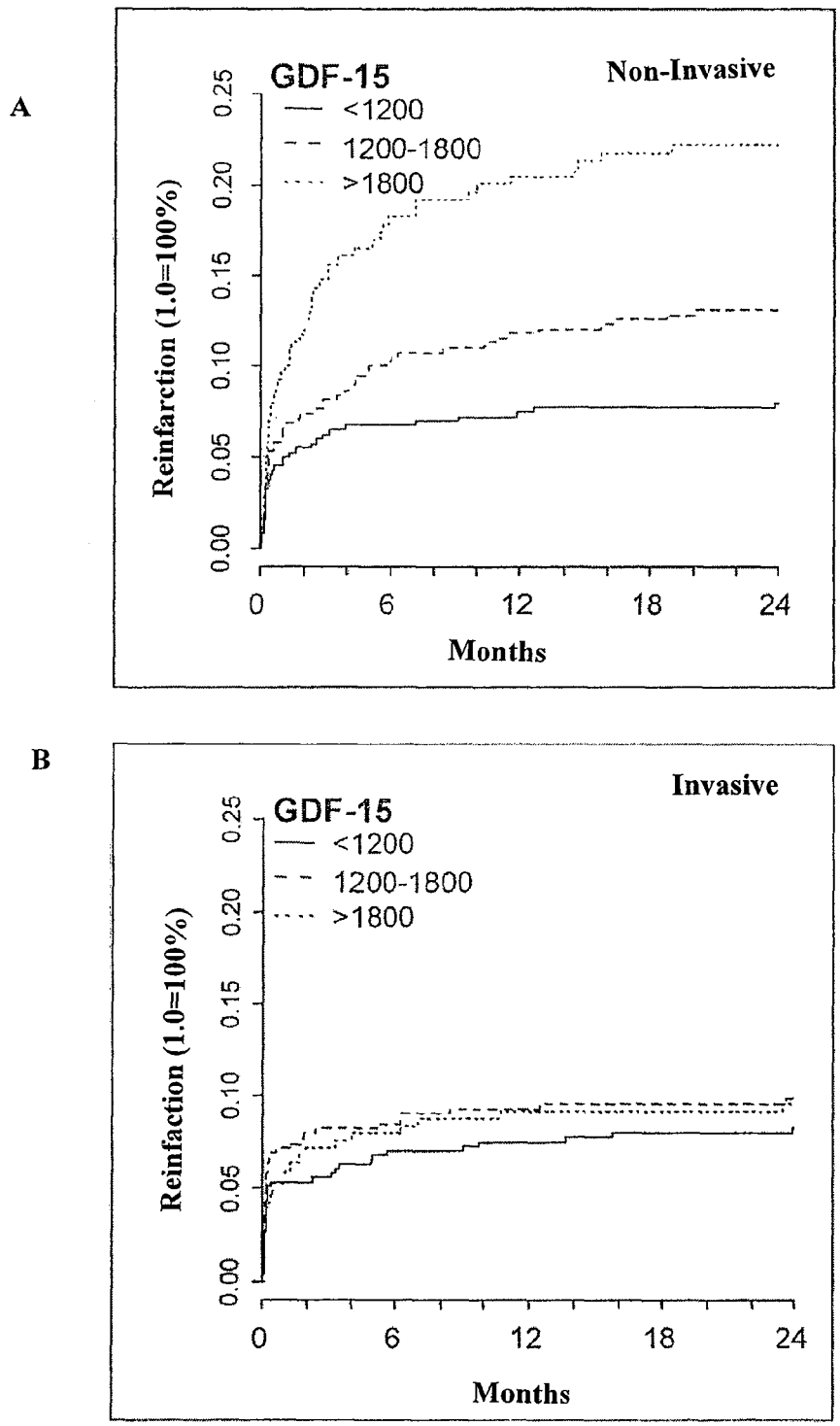
FIGS. 1 A-B illustrate cumulative probability of acute myocardial infarction during 2 years according to tertiles of GDF-15 levels on admission in (A) 1034 non-invasive NSTE-ACS patients (1200 n=400, 1200-1800 n=394, 0.1800 n=240) enrolled in the FRISC II trial (P, 0.0001 by log-rank test), and (B) 1045 invasive NSTE-ACS patients (,1200 n=416, 1200-1800 n=376, 0.1800 n=253) enrolled in the FRISC II trail (P=0.6915 by log-rank test).

The term "identifying" as used herein means assessing whether a subject will be susceptible for a cardiac intervention or not. As will be understood by those skilled in the art, such an assessment is usually not intended to be correct for all (i.e., 100%) of the subjects to be identified. The term, however, requires that a statistically significant portion of subjects can be identified (e.g., a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% of at least 99%. The p-values are, preferably, 0.1, 0.05, 0.01, 0.005, or 0.0001. More preferably, at least 60%, at least 70%, at least 80% or at least 90% of the subjects of a population can be properly identified by the method of the present invention.

The term "subject" as used herein relates to animals, preferably mammals, and, more preferably, humans. However, it is envisaged in accordance with the aforementioned method of the present invention that the subject shall be "in need of a cardiac intervention", i.e., exhibit symptoms and/or physical signs known to be associated with an acute cardiovascular event, e.g., chest discomfort, dyspnea, ECG changes and others as described above. More preferably, the subject shall exhibit one or more episodes of angina lasting at least 5 min within the preceding 24 h, and have either a positive cardiac troponin T or I test or at least 0-5 mm of transient or persistent ST-segment depression not known to be preexisting and not attributable to coexisting disorders. Alternatively but nevertheless also preferably, the subject shall exhibit symptoms of ischemia that were increasing or occurring at rest, or that warranted the suspicion of acute myocardial infarction, with the last episode within the preceding 48 h. Myocardial ischemia had to be verified by electrocardiography (ST depression=0·1 mV or T-wave inversion=0·1 mV) or by raised biochemical markers (creatine kinase [CK]-MB>6 μg/L, troponin-T>0.01 ng/ml, qualitative troponin-T test positive, or catalytic activity of CK, CK-B, or CK MB higher than the local diagnostic limit for myocardial infarction).

Acute cardiovascular events are, preferably, acute coronary syndromes (ACS). ACS patients can show unstable angina pectoris (UAP) or myocardial infarction (MI). MI can be an ST-elevation MI (STEMI) or a non-ST-elevated MI (NSTEMI). The occurring of an ACS can be followed by a left ventricular dysfunction (LVD) and symptoms of heart failure.

The term "cardiac intervention" encompasses those treatment regimens which comprise an intervention by surgery, microsurgery or other invasive therapies affecting the cardiovascular system and, preferably, the heart. Preferably, cardiac interventions as used herein are treatment regimens which aim to restore the proper oxygen supply of the heart. This is, preferably, achieved by restoring the blood flow throughout the blood vessels supporting the heart, i.e., the coronary blood vessels. Those blood vessels may be impaired due to, e.g., thrombotic or atherosclerotic plaques. Accordingly, cardiac interventions shall, preferably, comprise a destruction and/or removal of such plaques and a restoration of the vessel, if necessary. Preferred cardiac interventions in accordance with the present invention are selected from the group consisting of percutaneous coronary angioplasty, percutaneous transluminal coronary balloon angioplasty, laser angioplasty, coronary stent implantation, bypass implantation or intraluminal techniques aiming to restore blood flow, vessel patency, stabilize plaque, and/or reduce intracoronary thrombus load.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

The term "growth differentiation factor-15" or "GDF-15" relates to polypeptide being a member of the transforming growth factor (TGF)-β cytokine superfamily. The terms polypeptide, peptide, and protein are used interchangeably throughout this specification. GDF-15 was originally cloned as macrophage-inhibitory cytokine-1 and later also identified as placental transforming growth factor-β, placental bone morphogenetic protein, non-steroidal anti-inflammatory drug-activated gene-1, and prostate-derived factor (Bootcov loc cit; Hromas, 1997 Biochim Biophys Acta 1354:40-44; Lawton 1997, Gene 203:17-26; Yokoyama-Kobayashi 1997, J Biochem (Tokyo), 122:622-626; Paralkar 1998, J Biol Chem 273:13760-13767). Similar to other TGF-β-related cytokines, GDF-15 is synthesized as an inactive precursor protein, which undergoes disulfide-linked homodimerization. Upon proteolytic cleavage of the N-terminal pro-peptide, GDF-15 is secreted as a ~28 kDa; dimeric protein (Bauskin 2000, Embo J 19:2212-2220). Amino acid sequences for GDF-15 are disclosed in WO99/06445, WO00/70051, WO2005/113585, Bottner 1999, Gene 237: 105-111, Bootcov loc. cit, Tan loc. cit., Baek 2001, Mol Pharmacol 59: 901-908, Hromas loc cit, Paralkar loc cit, Morrish 1996, Placenta 17:431-441 or Yokoyama-Kobayashi loc cit. GDF-15 as used herein encompasses, also variants of the aforementioned specific GDF-15 polypeptides. Such variants have at least the same essential biological and immunological properties as the specific GDF-15 polypeptides. In particular, they share the same essential biological and immunological properties if they are detectable by the same specific assays referred to in this specification, e.g., by ELISA assays using polyclonal or monoclonal antibodies specifically recognizing the said GDF-15 polypeptides. A preferred assay is described in the accompanying Examples. Moreover, it is to be understood that a variant as referred to in accordance with the present invention shall have an amino acid sequence which differs due to at least the one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific GDF-15 polypeptides. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identify. Preferably, the default values of 5.00 for gap weight and 0.30 for gap weight length are used. Variants referred to above may be allelic variants or any other species specific homologs, paralogs, or orthologs. Moreover, the variants referred to herein include fragments of the specific GDF-15 polypeptides or the aforementioned types of variants as long as these fragments have the essential immunological and biological properties as referred to above. Such fragments may be, e.g., degradation products of the GDF-15 polypeptides. Further included are variants which differ due to post-translational modifications such as phosphorylation or myristylation.

Determining the amount of GDF-15 or any other peptide or polypeptide referred to in this specification relates to measuring the amount or concentration, preferably semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e., a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the peptide or polypeptide. Moreover, the signal strength can, preferably, be correlated directly or indirectly (e.g., reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on ELECSYS analyzers, Roche Diagnostics GmbH), CBA (an enzymatic cobalt binding assay, available, for example, on Roche-Hitachi analyzers, Roche Diagnostics GmbH), and latex agglutination assays (available, for example, on Roche-Hitachi analyzers).

Preferably, determining the amount of a peptide or polypeptide comprises the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g., a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprises the steps of (a) contacting the peptide with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g., nucleic acid or peptide aptamers. Methods to prepare such ligands are well-known in the art. For example, identification and production of suitable antibodies of aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g., phage display. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide of polypeptide should be bound with at least 3 times higher, more preferably at least 10 times higher and even more preferably at least 50 times higher affinity than any other relevant peptide of polypeptide. Non-specific binding may be tolerable, if it can still be distinguished and measured unequivocally, e.g., according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g., by NMR or surface plasmon resonance.

Second, if the ligand also serves as a substrate of an enzymatic activity of the peptide or polypeptide of interest, an enzymatic reaction product may be measured (e.g., the amount of a protease can be measured by measuring the amount of cleaved substrate, e.g., on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable lable prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-tag, glutathione-S-transferase, FLAG, GFP, myc-tag, influenza A virus haemagglutinin (HA), maltose binding protein, and the like. In the case of a peptide of polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels (e.g., "magnetic beads", including paramagnetic and superparamagnetic labels), and fluorescent labels. Enzymatically active labels include, e.g., horseradish peroxidase, alkaline phosphatase; beta-galactosidase, luciferase, and derivatives thereof. Suitable substrates for detection include diamino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star (Amersham Biosciences), ECF (Amersham Biosciences). A suitable enzyme-substrate combination may result in a colored reaction product, fluorescence or chemiluminescence, which can be measured according to methods known in the art (e.g., using a light-sensitive film of a suitable camera system). As for measuring the enzymatic reaction, the criteria given above apply analogously. Typical fluorescent labels include fluorescent proteins (such as GFP and its derivatives); Cy3, Cy5, Texas Red, Fluorescein, and the Alexa dyes (e.g., Alexa 568). Further fluorescent labels are available, e.g., from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g., a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoroimmunoassay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamide gel electrophoresis (SDS-PAGE), Western Blotting, and mass spectrometry), can be used alone or in combination with labeling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinylchloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions, and the like. It is also contemplated to use "suspension arrays" as arrays according to the present invention (Nolan 2002, Trends Biotechnol. 20(1):9-12). In such suspension arrays, the carrier, e.g., a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide, the relative amount or concentration of the said polypeptide or peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of the peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e., automatically provide the desired assessment in a suitable output format. Based on the comparison of the amount determined in step a) and the reference amount, it is possible to assess whether a subject is susceptible for a cardiac intervention, i.e., belonging to the group of subjects which can be successfully treated by the cardiac intervention. Therefore, the reference amount is to be chosen so that either a difference or a similarity in the compared amounts allows identifying those the test subject which belong into the group of subjects susceptible for cardiac intervention or identifying those test subjects which are not susceptible for a cardiac intervention.

Accordingly, the term "reference amount" as used herein refers to an amount which allows assessing whether a subject in need thereof will be susceptible for a cardiac intervention as referred to above. Accordingly, the reference may either be derived from (i) a subject known to have been successfully treated, i.e., without the occurrence of adverse effects such as re-infarction or mortality or side effects caused by the treatment regimen, or (ii) a subject known to have been not successfully treated, i.e., a subject which developed re-infarction or which died due to cardiovascular complications after a cardiac intervention or did not derive benefit from the treatment regimen. Moreover, the reference amount may define a threshold amount, whereby an amount larger than the threshold shall be indicative for a subject being susceptible for a cardiac intervention while an amount lower than the threshold amount shall be an indicator for a subject which can not be treated successfully by the cardiac intervention. The reference amount applicable for an individual subject may vary depending on various physiological parameters such as age, gender, or subpopulation, as well as on the means used for the determination of the polypeptide or peptide referred to herein. A suitable reference amount may be determined by the method of the present invention from a reference sample to be analyzed together, i.e., simultaneously or subsequently, with the test sample. A preferred reference amount serving as a threshold may be derived from the upper limit of normal (ULN), i.e., the upper limit of the physiological amount to be found in a population of apparently healthy subjects. The ULN for a given population of subjects can be determined by various well known techniques. A suitable technique may be to determine the median of the population for the peptide or polypeptide, amounts to be determined in the method of the present invention. A preferred threshold (i.e., reference amount) for GDF-15 is at least one to two times the ULN. The ULN referred to in this context is, preferably, 1200 pg/ml.

Thus, the reference amount defining a threshold amount for GDF-15 as referred to in accordance with the present invention is 1800 pg/ml or 2400 pg/ml and, more preferably, 1200 pg/ml.

An amount of GDF-15 larger than the reference amount is, more preferably, indicative for a subject being susceptible to a cardiac intervention.

Advantageously, it has been found in the study underlying the present invention that GDF-15 is a reliable prognostic biomarker for assessing the success of cardiac interventions for subjects in need thereof, i.e., subjects which suffer from cardiovascular complications and, in particular, those which are affected by acute cardiovascular events or heart failure. Thanks to the present invention, a risk/success stratification can be easily performed before subjecting a patient to a cardiac intervention. In case the patient turns out to be not susceptible for a cardiac intervention, said dangerous, time and/or cost intensive therapy can be avoided. Thus, besides preventing a subject from the adverse and severe side effects accompanying a cardiac intervention, the method of the present invention will be beneficial for the health system in that resources will be saved. It is to be understood that according to the method of the present invention described herein above and below, the amount of GDF-15 or means for the determination thereof can be used for the manufacture of a diagnostic composition for identifying a subject being susceptible for a cardiac intervention.

In addition or alternatively, the above method of the present invention may be used to identify a subject susceptible to a cardiac therapy, preferably a drug based therapy as specified below or an anti-platelet therapy.

In a preferred embodiment of the method of the present invention, said method further comprises determining the amount of a cardiac troponin in said sample of the subject and comparing the amount of the cardiac troponin to a reference amount.

The term "cardiac troponin" refers to all troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493.

Preferably, cardiac troponin refers to troponin T and/or troponin I, and, most preferably, to troponin T. It is to be understood that isoforms of troponins may be determined in the method of the present invention together, i.e., simultaneously or sequentially, or individually, i.e., without determining the other isoform at all. Amino acid sequences for human troponin T and human troponin I are disclosed in Anderson, loc cit and Ferrieres 1998, Clinical Chemistry, 44: 487-493.

The term "cardiac troponin" encompasses also variants of the aforementioned specific troponins, i.e., preferably, of troponin T or troponin I. Such variants have at least the same essential biological and immunological properties as the specific cardiac troponins. In particular, they share the same essential biological and immunological properties if they are detectable by the same specific assays referred to in this specification, e.g., by ELISA Assays using polyclonal or monoclonal antibodies specifically recognizing the said cardiac troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific troponin. Variants may be allelic variants or any other species specific homologs, paralogs, or orthologs. Moreover, the variants referred to herein include fragments of the specific cardiac troponins or the aforementioned types of variants as long as these fragments have the essential immunological and biological properties as referred to above. Such fragments may be, e.g., degradation products of the troponins. Further included are variants which differ due to posttranslational modifications such as phosphorylation or myristylation.

As discussed above already, a preferred reference amount serving as a threshold may be derived from the ULN. The ULN for a given population of subjects can be determined as specified elsewhere in this description. A preferred threshold (i.e., reference amount) for a cardiac troponin and, in particular for troponin T or I, is at least one times, more preferably two to five times the ULN. Preferably, the ULN for troponin T referred to in this context is 0.01 ng/ml and 0.1 ng/ml for troponin I.

Thus, the reference amount defining a threshold for troponin T as referred to in accordance with the present invention is, preferably, 0.01 ng/ml, 0.02 ng/ml of 0.05 ng/ml.

An amount of a cardiac troponin larger than the reference amount is, more preferably, indicative for a subject being susceptible to a cardiac intervention.

In a furthermore preferred embodiment of the method of the present invention, the method further (i.e., in addition to the determination of GDF-15 and/or a cardiac troponin) comprises determining the amount of a natriuretic peptide in said sample of the subject and comparing the amount of the natriuretic peptide to a reference.

The term "natriuretic peptide" comprises atrial natriuretic peptide (ANP)-type and brain natriuretic peptide (BNP)-type peptides and variants thereof having the same predictive potential. Natriuretic peptides according to the present invention comprise ANP-type and BNP-type peptides and variants thereof (see, e.g., Bonow, 1996, Circulation 93: 1946-1950). ANP-type peptides comprise pre-proANP, proANP, NT-proANP, and ANP. BNP-type peptides comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP).

Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NT-proBNP is 120 min longer than that of BNP, which is 20 min (Smith 2000, J Endocrinol. 167: 239-46). Preanalyses are more robust with NT-proBNP allowing easy transportation of the sample to a central laboratory (Mueller 2004, Clin Chem Lab Med 42: 942-4). Blood samples can be stored at room temperature for several days or may be mailed or shipped without recovery loss. In contrast, storage of BNP for 48 hours at room temperature of at 4° Celsius leads to a concentration loss of at least 20% (Mueller loc. cit.; Wu 2004, Clin Chem 50: 867-73). Therefore, depending on the time-course or properties of interest, either measurement of the active or the inactive forms of the natriuretic peptide can be advantageous.

The most preferred natriuretic peptides according to the present invention are NT-proBNP or variants thereof. As briefly discussed above, the human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NT-proBNP referred to in accordance with the present invention further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are immunological and/or biological properties. Preferably, the NT-proBNP variants have immunological properties (i.e., epitope composition) comparable, to those of NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Invest 59:177-181), Yeo et al. (Yeo 2003, Clinica Chimica Acta 338:107-115). Variants also include posttranslationally modified peptides such as glycosylated peptides. Further, a variant in accordance with the present invention is also a peptide or polypeptide which has been modified after collection of the sample, for example by covalent or non-covalent attachment of a label, particularly a radioactive or fluorescent label, to the peptide.

As discussed above already, a preferred reference amount serving as a threshold may be derived from the ULN. The ULN for a given population of subjects can be determined as specified elsewhere in this description. A preferred threshold (i.e., reference amount) for a natriuretic peptide and, in particular for NT-proBNP, is at least one times, more preferably two to four times the ULN. Preferably, the ULN for NT-proBNP referred to in this context is 300 pg/ml. ULNs for the other natriuretic peptides are known in the art and are, preferably, 40 pg/ml for ANP, 100 pg/ml for BNP and 500 pmol/l for NT-proANP.

Thus, the reference amount defining a threshold for NT-proBNP as referred to in accordance with the present invention is, preferably, 600 pg/ml or 1200 pg/ml and, more preferably, 1000 pg/ml.

An amount of a natriuretic peptide larger than the reference amount is, more preferably, indicative for a subject being susceptible to a cardiac intervention.

It is to be understood that the definitions and explanations of the terms made above and below apply accordingly for all embodiments described in this specification and the accompanying claims.

The present invention further relates to a method of identifying a subject being susceptible to a therapy of heart failure comprising
  (a) determining the amount of growth differentiation factor 15 (GDF-15) in a sample of a subject in need of a therapy of heart failure; and
  (b) comparing the amount of GDF-15 determined in step a) to a reference amount, whereby a subject being susceptible to a therapy of heart failure is to be identified.

The term "heart failure (HF)" as used herein refers to an impaired systolic and/or diastolic function of the heart. Preferably, the term relates to congestive heart failure which may be caused by various underlying diseases or disorders. Preferably, heart failure referred to herein is also chronic heart failure. Heart failure can be classified into a functional classification, system according to the New York Heart Association (NYHA). Patients of NYHA class I have no obvious symptoms of cardiovascular disease but already have objective evidence of functional impairment. Physical activity is not limited, and ordinary physical activity does not cause undue fatigue, palpitation, or dyspnea (shortness of breath). Patients of NYHA class II have slight limitation of physical activity. They are comfortable at rest, but ordinary physical activity results in fatigue, palpitation, or dyspnea. Patients of NYHA class III show a marked limitation of physical activity. They are comfortable at rest, but less than of ordinary activity causes fatigue, palpitation, or dyspnea. Patients of NYHA class IV are unable to carry out any physical activity without discomfort. They show symptoms of cardiac insufficiency at rest.

It is to be understood that the subject to be identified by the aforementioned method, preferably, has objective evidence of impaired systolic and/or diastolic function of the heart as shown, for example, by echocardiography, angiography, szintigraphy, or magnetic resonance imaging. This functional impairment can be accompanied by symptoms of heart failure as outlined above (NYHA class II-IV), although some patients may present without significant symptoms (NYHA I.

Preferably, the said therapy to be selected for a subject by the method of the present invention said therapy is a drug-based therapy. More preferably, the said medicament is an ACE inhibitor, preferably captopril, enalapril, fosinopril, lisinopril, perindopril, quinapril, ramipril, or trandolapril, an AT-1 receptor blocking agent, preferably, candesartan, losartan, or valsartan, a β-receptor blocking agent, preferably, bisoprolol, carvedilol, metoprolol or succinate, or an aldosterone antagonist, preferably, spironolacton or eplerenone.

Another preferred therapy to be selected for a subject in accordance with the present invention is an interventional therapy. An interventional therapy as referred to herein is a therapy which is based on physical interventions with the subject, e.g., by surgery, and/or electrophysiological interventions. More preferably, said interventional therapy is cardiac resynchronization therapy (CRT) or based on implantation of a cardioverter defibrillator (ICD).

Advantageously, by determining the GDF-15 amount in a sample of a subject suffering from heart failure, it can be decided whether a subject will be susceptible for a therapy as referred to above. Specifically, it is envisaged that a subject having an amount of GDF-15 larger than the reference amount will be suitable to be treated by the aforementioned therapy while a subject with less GDF-15 will not benefit from the therapy.

The present invention, furthermore, relates to a method for predicting the risk of mortality or a further acute cardiovascular event for a subject suffering from a cardiovascular complication comprising
  (a) determining the amounts of GDF-15 and a natriuretic peptide and/or a cardiac troponin in a sample of a subject; and
  (b) comparing the amounts of GDF-15 and the natriuretic peptide and/or the cardiac troponin determined in step a) to reference amounts, whereby the risk of mortality or a further cardiovascular event is to be predicted.

The term "predicting" used herein refers to assessing the probability according to which a subject suffering from a cardiovascular complication will die (i.e., mortality caused by the cardiovascular complication) or develop an acute cardiovascular event, such as myocardial (re)-infarction, within a defined time window (predictive window) in the future. The predictive window is an interval in which the subject will develop an acute cardiovascular event of will die according to the predicted probability. The predictive window may be the entire remaining lifespan of the subject upon analysis by the method of the present invention. Preferably, however, the predictive window is an interval of one month, six months or one, two, three, four, five or ten years after appearance of the cardiovascular complication (more preferably and precisely, after the sample to be analyzed by the method of the present invention has been obtained). As will be understood by those skilled in the art, such an assessment is usually not intended to be correct for 100% of the subjects to be analyzed. The term, however, requires that the assessment will be valid for a statistically significant portion of the subjects to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction will be correct for at least 60%, at least 70%, at least 80%, or at least 90% of the subjects of a given cohort.

The term "mortality" as used herein relates to mortality which is caused by the said cardiovascular complication, e.g., as a result of myocardial (re-)infarction.

The term "cardiovascular complication" as used herein refers to any chronic disorder of the cardiovascular system or any acute cardiovascular event. Preferably, a chronic disorder of the cardiovascular system as used herein encompasses coronary heart diseases, stable angina pectoris (SAP) or heart failure, preferably chronic heart failure. Acute cardiovascular events are, preferably, acute coronary syndromes (ACS). ACS patients can show unstable angina pectoris (UAP) or myocardial infarction (MI). MI can be an ST-elevation MI (STEMI) or a non-ST-elevation MI (NSTEMI). NSTE-ACS as used herein encompasses UAP and NSTEMI. The occurring of an MI can be followed by a left ventricular dysfunction (LVD), of development of heart failure. Further preferred cardiovascular complications encompass cardiac brady- or tachyarrhythmias including sudden cardiac death and stroke (cerebrovascular events or accidents). Most preferably, the said cardiovascular complication is ACS or heart failure.

The expression "predicting the risk of mortality or a further (i.e., recurrent) acute cardiovascular event" as used herein means that it the subject to be analyzed by the method of the present invention is allocated either into the group of subjects of a population having a normal, i.e., non-elevated, risk for developing an acute cardiovascular event or mortality following a cardiovascular complication or into a group of subjects having a significantly elevated risk. An elevated risk as referred to in accordance with the present invention means that the risk of developing a further acute cardiovascular event or the risk of mortality within a predetermined predictive window is elevated significantly for a subject with respect to the average risk for an acute cardiovascular event of cardiac mortality in a population of subjects. Preferably, for a predictive window of one year, the average risk is within the range of 0.5 and 3.0%, preferably, 1.5%. An elevated risk as used herein, preferably, relates to a risk of more than 3.0%, preferably, more than 5.0%, and, most preferably within 3.0% and 8.0% with respect to a predictive window of one year.

Advantageously, it has been found an the studies underlying the present invention that determining either (i) the amounts of GDF-15 and a natriuretic peptide or (ii) GDF-15 and a cardiac troponin or, preferably, (iii) the amounts of GDF-15, a natriuretic peptide and a cardiac troponin are required for a reliable assessment of the risk of mortality or a further adverse acute cardiovascular event in a subject suffering already from a cardiovascular disease. The aforementioned method is more reliable than those of the prior art since it has been found that GDF-15 and natriuretic peptides such as NT-proBNP are statistically independent predictors. Specifically, the GDF-15 level (i.e., the amount) in apparently healthy elderly subjects varied between 450 pg/ml (rounded 10th percentile) and 1200 pg/ml (rounded 90th percentile, defined as the upper limit of normal) with a median of 762 pg/ml. Compared to healthy individuals, about two thirds of NSTE-ACS patients had levels; above the upper limit, of normal, and one third had levels above 1800 pg/ml. Among patients within the normal range of GDF-15, 1-year mortality was low at 1.5%. In those with a moderate elevation of GDF-15 (1200 to 1800 pg/ml) 1-year mortality was elevated at 5.0%, while in those patients with a marked elevation (>1800 pg/ml), 1-year mortality was very high at 14.1%. The differences in mortality were observed early after the index event and highly significant already after one month. Receiver operating characteristic (ROC) curve analyses further illustrated that GDF-15 is a strong biochemical marker of 1-year mortality with an area under the curve of 0.757. By multiple regression analysis, the GDF-15 level on admission was inversely related to the time from symptom onset to admission (delay time) in NSTE-ACS. This finding might be related to the association between the GDF-15 level and the severity of disease/symptoms leading to a shorter delay time in patients with higher GDF-15 levels. Although the median GDF-15 level increased slightly after admission, it remained remarkably stable within each patient during 72 hours of observation. GDF-15 levels determined in individual patients at different occasions were closely correlated, and gave similar prognostic information about mortality, showing that a single measurement of GDF-15 obtained after admission will provide comparable prognostic information in patients with NSTE-ACS. The verification of the prognostic information in the GDF-15 levels at all four time points in patients with NSTE-ACS supports the reliability of these findings. GDF-15 levels in NSTE-ACS patients were strongly and independently related to age, current smoking, diabetes, history of heart failure, cardiac dysfunction (NT-proBNP), inflammatory activity (CRP), and renal dysfunction (creatinine clearance), indicating that elevated levels of GDF-15 integrate several important clinical and biochemical indicators of more severe cardiovascular disease and poor prognosis in patients with NSTE-ACS. Out of all these interrelated variables, GDF-15 emerged as the strongest predictor of raised 1-year mortality. Beyond GDF-15, only age, previous myocardial infarction, and the levels of NT-proBNP added independent prognostic information about mortality. Similarly, it has been found that the GDF-15 levels provide reliable prognostic information on recurrent MI; see FIG. 1 and Table 1, below. Thanks to this aspect of the present invention, a risk stratification for patients suffering already from cardiovascular complications can be more reliably performed. It is to be understood that according to the method of the present invention described herein above and below, the amount of GDF-15 and either a natriuretic peptide, a cardiac troponin or a combination thereof or means for the determination thereof can be used for the manufacture of a diagnostic composition for predicting the risk of mortality or a further acute cardiovascular event for a subject suffering from a cardiovascular complication.

Moreover, it has been found that the method of the present invention comprising the determination of GDF-15 and a natriuretic peptide can be, preferably, used for the determination of the risk for mortality while a combination of GDF-15 and a cardiac troponin can be, preferably, used for predicting the risk for a further acute cardiovascular event. Accordingly, the present invention also encompasses to a method for predicting the risk of mortality for a subject suffering from a cardiovascular complication comprising determining the amounts of GDF-15 and a natriuretic peptide in a sample of a subject; and comparing the amounts of GDF-15 and the natriuretic peptide determined in the previous step to reference amounts. Furthermore, the present invention relates to a method for predicting the risk for a further acute cardiovascular event for a subject suffering from a cardiovascular complication comprising determining the amounts of GDF-15 and a cardiac troponin in a sample of a subject; and comparing the amounts of GDF-15 and the cardiac troponin determined in the previous step to reference amounts.

In a preferred embodiment of the method of the present invention, the said reference amount (i.e., the threshold amount) for GDF-15 is 1200 pg/ml. More preferably, an amount of GDF-15 larger than the reference is indicative for an elevated risk of mortality or a further acute cardiovascular event.

In a further preferred embodiment of the method of the present invention, the said reference amount (i.e., the threshold amount) for troponin T is 0.01 ng/ml.

More preferably, an amount of the cardiac troponin larger than the reference amount is indicative for an elevated risk of mortality or a further acute cardiovascular event.

In another preferred embodiment of the method of the present invention, the said reference amount (i.e., the threshold amount) for NT-proBNP is 1000 pg/ml.

More preferably, an amount for the natriuretic peptide larger than the reference amount is indicative for an elevated risk of mortality or a further acute cardiovascular event.

The present invention, furthermore, encompasses a method for predicting the risk of an adverse cardiovascular complication for a subject suffering from heart failure comprising (a) determining the amounts of GDF-15 in a sample of a subject and (b) comparing the amounts of GDF-determined in step a) to a reference amount.

It has been found in the studies underlying the present invention that a subject exhibiting the symptoms of heart failure and, preferably, suffering from chronic heart failure, has an increased risk for adverse cardiovascular complication, preferably, a future acute cardiovascular event or, more preferably, mortality. Among various biomarkers which have been investigated in the said study, GDF-15 turned out to be an independent predictor for an increased risk of adverse cardiovascular complications and, in particular, mortality as specified above.

The present invention, furthermore, relates to a method for predicting the risk of mortality or a subsequent pulmonary embolism-related complication for a subject suffering from pulmonary embolism comprising (a) determining the amounts of GDF-15 in a sample of a subject; and
(b) comparing the amount of GDF-15 determined in step a) to a reference amount, whereby the risk of mortality or a subsequent pulmonary embolism-related complication is to be predicted.

The term "pulmonary embolism" as used herein refers to a disorder caused by occlusion or stenosis of blood vessels of the lung. As a result of the said occlusion or stenosis, gas exchange and blood supply of the pulmonary tissue will become impaired. Thus, the physiological function of the lung becomes impaired. Pulmonary embolism as used herein may be chronic or acute pulmonary embolism. Preferably, the term, however, refers to acute pulmonary embolism. Pulmonary embolism can be diagnosed by well known diagnostic techniques and is accompanied by symptoms as described in standard medical text books.

A "subsequent pulmonary embolism-related complication" as referred to in accordance with the present invention is an adverse event and, preferably a cardio-pulmonary event, including a further pulmonary embolism or any other impairment of the physiological function of the lung or the cardiovascular system which requires intervention such as incubational measures, catecholamine administration or cardiopulmonary reanimation. The subsequent pulmonary embolism-related complication shall occur within the predictive time window after the primary pulmonary embolism the subject is suffering from.

The expression "predicting the risk of mortality" as used herein means that it the subject to be analyzed by the method of the present invention is allocated either into the group of subjects of a population having a normal, i.e., non-elevated, risk for mortality following pulmonary embolism or into a group of subjects having a significantly elevated risk. An elevated risk as referred to in accordance with the present invention means that the risk of mortality within a predetermined predictive window is elevated significantly for a subject with respect to the average risk for mortality in a population of subjects. Preferably, for a predictive window of 30 days, the average risk is about 5.0%. An elevated risk as used herein, preferably, relates to a at least 5-times increased risk or, preferably, an at least 10-times increased risk, i.e., a risk of more than 50.0%. Moreover, the term also relates to a significant increased risk within a predictive window of six month. The normal risk of mortality within said predictive window is, preferably, at least 5-times, more preferably, 7-times increased in a subject being at risk of mortality as meant herein.

The reference amount defining a threshold in the context of predicting whether a subject is at risk of mortality or a subsequent pulmonary embolism-related complication is, preferably, 4,600 pg/ml. A sample having an amount of more than 4,600 pg/ml shall indicate that a subject of which the sample has been derived is at risk of mortality or a subsequent pulmonary embolism-related complication as referred to above, while an amount of less than 4,600 pg/ml indicates that a subject is not at risk.

In principle, it has been found that GDF-15 or means for determining the amount of GDF-15 can be used for the manufacture of a diagnostic composition for predicting whether a subject suffering from pulmonary embolism is at risk of mortality or a subsequent pulmonary embolism-related complication.

Advantageously, it has been found in the studies underlying the present invention that risk stratification for subjects suffering from pulmonary, embolism can be reliably made based on GDF-15 as a biomarker. Based on said risk stratification, if may be decided which further measures such as specific therapies shall be applied to a subject and which degree of clinical monitoring will be required.

In a preferred embodiment of the aforementioned method of the present invention, GDF-15 will be determined together with other markers of embolism, preferably, a cardiac troponin and/or a natriuretic peptide as referred to elsewhere in this specification.

Encompassed by the present invention is, further, a device for identifying a subject being susceptible to a cardiac intervention or a therapy for heart failure adapted to carry out the method of the present invention comprising means for determining the amount of GDF-15 in a sample of the subject and means for comparing said amount to a reference amount, whereby a subject being susceptible to a cardiac intervention or a therapy for heart failure is identified.

The term "device" as used herein relates to a system of means comprising at least the aforementioned means operatively linked to each other as to allow the prediction. Preferred means for determining the amount of GDF-15, preferably, in combination with a cardiac troponin and/or a natriuretic peptides, and means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to obtain the desired results. Preferably, the means are comprised by a single device in such a case. Said device may accordingly include an analyzing unit for the measurement of the amount of the peptides or polypeptides in an applied sample and a computer unit for processing the resulting data for the evaluation. Alternatively, where means such as test strips are used for determining the amount of the peptides or polypeptides, the means for comparison may comprise control strips or tables allocating the determined amount to a reference amount. The test strips are, preferably, coupled to a ligand which specifically binds to the peptides or polypeptides referred to herein. The strip or device, preferably, comprises means for detection of the binding of said peptides or polypeptides to the said ligand. Preferred means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test strips or electronic devices which merely require loading with a sample. The results may be given as output of raw data, which need interpretation by the clinician. Preferably, the output of the device is, however, processed, i.e., evaluated, raw data the interpretation of which does not require a clinician. Further, preferred devices comprise the analyzing units/devices (e.g., biosensors, arrays, solid supports coupled to ligands specifically recognizing the natriuretic peptide, Plasmon surface resonance devices, NMR spectrometers, mass-spectrometers etc.) or evaluation units/devices referred to above in accordance with the method of the invention.

Moreover, the present invention also relates to a device for predicting the risk of mortality or a further acute cardiovascular event for a subject adapted to carry out the method of the present invention comprising means for determining the amount of GDF-15 and a natriuretic peptide and/or a cardiac troponin in a sample of a subject and means for comparing said amounts to reference amounts, whereby it is predicted whether a subject is at risk of mortality or a further acute cardiovascular event.

Further envisaged is a device for predicting the risk of an adverse cardiovascular complication for a subject suffering from heart failure adapted to carry out the method of the present invention comprising means for determining the amount of GDF-15 in a sample of the said subject and means for comparing said amount to preference amount, whereby it is predicted whether a subject is at risk of an adverse cardiovascular complication.

The present invention also relates to a device for predicting whether a subject suffering from pulmonary embolism is a risk of mortality or a subsequent pulmonary embolism-related complication adapted to carry out the method of the present invention comprising-means for determining the amount of GDF-15, preferably, in combination with a natriuretic peptide and/or a cardiac troponin in a sample of a subject suffering from pulmonary embolism and means for comparing said amounts to reference amounts, whereby it is predicted whether a subject is at risk of mortality or a subsequent pulmonary embolism-related complication.

Furthermore, a kit for carrying out the method of the present invention for identifying a subject being susceptible to a cardiac intervention or a therapy for heart failure is envisaged by the present invention. Said kit comprising means for determining the amount of GDF-15 in a sample of a subject and means for comparing said amounts to reference amounts, whereby a subject being susceptible to a cardiac intervention or a therapy for heart failure is identified.

The term "kit" as used herein refers to a collection of the aforementioned means, preferably, provided in separately or within a single container. The container, also preferably, comprises instructions for carrying out the method of the present invention.

The present invention pertains to a kit for carrying out the method of the present invention for predicting the risk of mortality or a further acute cardiovascular event comprising means for determining the amount of GDF-15 and a natriuretic peptide and/or a cardiac troponin in a sample of a subject and means for comparing said amounts to reference amounts, whereby it is predicted whether a subject is at risk of mortality or a further acute cardiovascular event.

Also, the present invention relates to a kit for carrying out the method of the present invention for predicting the risk of an adverse cardiovascular complication comprising means for determining the amount of GDF-15 in a sample of a subject suffering from heart failure and means for comparing said amount to a reference amount, whereby it is predicted whether a subject is at risk of an adverse cardiovascular complication.

Finally, the present invention relates to a kit for predicting whether a subject suffering from pulmonary embolism is a risk of mortality or a subsequent pulmonary embolism-related complication adapted to carry out the method of the present invention comprising means for determining the amount of GDF-15, preferably, in combination with a natriuretic peptide and/or a cardiac troponin in a sample of a subject suffering from pulmonary embolism and means for comparing said amounts to reference amounts, whereby it is predicted whether a subject is at risk of mortality or a subsequent pulmonary embolism-related complication.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

SPECIFIC EMBODIMENTS

Example 1

Determination of GDF-15, NT-proBNP and Troponin in Serum and Plasma Samples

To determine the concentration of GDF-15 in serum and plasma samples, a immunoradiometric assay (IRMA) using a polyclonal, GDF-15 affinity chromatography-purified, goat anti-human GDF-15 IgG antibody from R&D Systems (AF957) was developed. Maxisorp Startubes (Nunc) were coated overnight at 4° C. with 0.5 µg anti-GDF-15 IgG in 0.1 M Na-carbonate buffer (pH 9.0), and then washed twice with phosphate-buffered saline with 0.1% TWEEN 20 (ICI Americas Inc.). Serum or plasma samples (100 µl) were diluted 1:1 with assay buffer (30 g/l BSA, 10 g/l bovine IgG, 1% goat serum, 0.1% Na-azide, 1 M NaCl, 40 mM Na phosphate buffer, pH 7.4), added to the tubes, and incubated for 16 hours at 4° C. After two washing steps, 10 ng of [125I]-iodinated anti-GDF-15 IgG (specific activity 0.74 MBq/µg) were diluted in 200 µl assay buffer, added to each tube, and incubated for 4 hours at room temperature. After three final washing steps, bound radioactivity was quantified in a gamma counter (LKB Wallac 1261). In each experiment, a standard curve was generated with recombinant human GDF-15 from R&D Systems (957-GD/CF). The results with new batches of recombinant GDF-15 protein were tested in standard plasma samples and any deviation above 10% was corrected by introducing an adjustment factor for this assay. GDF-15 measurements in serum and plasma samples from the same patient yielded virtually identical results after correction for eventual dilution factors. The detection limit of the assay was 20 pg/ml. The intraassay coefficient of variation determined for mean GDF-15 levels of 744, 1518, and 8618 pg/ml was 5.6, 5.9, and 6.5%, respectively. The inter-assay coefficient of variation determined for mean GDF-15 levels of 832, 4739, and 9230 pg/ml was 8.6, 5.7, and 4.4%, respectively.

Troponin T levels were determined by a third-generation assay on an ELECSYS 2010 analyzer (Roche Diagnostics GmbH) with a detection limit 0.01 ng/ml.

NT-proBNP levels were determined with an immunoassay on an ELECSYS 2010 with a detection limit of 20 pg/ml.

Example 2

Analysis of Patients with NSTE-ACS of the FRISC II Study for Differences between Invasive and Non-Invasive Treatment Regimens Patients were recruited into the FRISC II study between June 1996, and May 1998 in 58 Scandinavian hospitals, 16 of which were interventional centers. Patients were eligible for inclusion if they had symptoms of ischemia that were increasing or occurring at rest, or that warranted the suspicion of acute myocardial infarction, with the last episode within 48 h before the start of dalteparin or standard heparin treatment. Myocardial ischemia had to be verified by electrocardiography (ST depression≥0·1 mV or T-wave inversion≥0·1 mV) or by raised biochemical markers (creatine kinase [CK]-MB>6 µg/L, troponin-T>0.10 µg/L, qualitative troponin-T test positive, or catalytic activity of CK, CK-B, or CK MB higher than the local diagnostic limit for myocardial infarction). Exclusion criteria were raised risk of bleeding episodes, anemia, or indication for or treatment in the past 24 h with thrombolysis, angioplasty in the past 6 months, being oh a waiting list for coronary revascularization, other acute or severe cardiac disease, renal or hepatic insufficiency, known clinically relevant osteoporosis, other severe illness, hypersensitivity to randomized drugs, anticipated difficulties with cooperation or participation in this or another clinical trial. Patients with previous open-heart surgery, advanced age (e.g., >75 years), or other disorders that made randomization to early revascularization inappropriate. The FRISC II, study was a prospective, randomized, multicentre trial with parallel groups. We compared invasive and non-invasive treatments by factorial design. Half of the patients in each group were randomly assigned long-term treatment with subcutaneous dalteparin of placebo for 3 months. The comparison of the invasive and non-invasive strategies was open and the comparison of long-term dalteparin treatment with placebo was double-blind.

In the invasive groups, the target was to perform all invasive procedures within 7 days of starting open-label dalteparin. The direct invasive treatments were coronary angiography within a few days of enrolment, aiming for revascularization within 7 days of the start of open-label treatment. Revascularization was recommended in all patients with an obstruction of at least 70% of the diameter of any artery supplying a substantial proportion of the myocardium. Percutaneous coronary intervention was recommended if there were one or two target lesions, and coronary-artery bypass surgery was preferred in patients with three-vessel or left main-artery disease.

Non-invasive treatment included coronary angiography in patients with refractory or recurrent symptoms, despite maximum medical treatment, or severe ischemia on a symptom-limited exercise test before discharge. The exercise-test criteria for performing angiography and revascularization were: ST depression≥0·3 mV; limiting chest pain associated with a low maximum work load (<90 W in men or <70 W in women) or a decrease in blood pressure; or ST elevation without preceding concomitant Q waves, or T-wave inversion on exercise testing. During long-term follow-up, invasive procedures were considered, irrespective of randomized strategy, for all patients with incapacitating symptoms, recurrence of instability, or myocardial infarction.

On admission, patients were initially treated with open-label subcutaneous dalteparin or standard heparin infusion adjusted for activated partial thromboplastin time. From randomization, all patients received dalteparin, 120 IU/kg every 12 h subcutaneously (maximum dose 10 000 IU), for at least 5 days in the non-invasive group and until procedures were done in the invasive group. Thereafter, patients received twice-daily subcutaneous injections of dalteparin or placebo. Women who weighed less than 80 kg and men who weighed less than 70 kg received 5000 IU dalteparin or placebo, and those who weighed more than these values received 7500 IU. This regimen was continued for 3 months, with patients self-injecting from prefilled single-dose syringes after discharge from hospital. The last injection of open-label or double-blind dalteparin treatment was given no later than 12 h before coronary procedures. After angioplasty, dalteparin or placebo were restarted 2-6 h after sheath removal. After administration of an infusion of the glycoprotein IIb/IIIa inhibitor abciximab, dalteparin or placebo were not restarted until 24 h after infusion. After coronary-artery bypass surgery, all patients received open-label dalteparin 5000 IU twice daily until mobilization, and double-blind treatment was started a few days before discharge. The compliance was monitored by asking patients to record all injections in diaries and by counting returned or unused syringes at outpatient visits. Aspirin was administered to all patients on admission at an initial dose of 300-600 mg, followed by a maintenance dose of 75-320 mg once daily. β-blockade was given unless contraindicated. Organic nitrates and calcium antagonists could be added as required. Lowering of cholesterol with statins, angiotensin converting-enzyme inhibitors for left-ventricular dysfunction, and aggressive antidiabetic treatment were recommended according to modern treatment guidelines. The use of abciximab was encouraged during percutaneous coronary interventions. Ticlopidine was recommended for 3-4 weeks after stent placement. On admission, or at the latest at randomization, blood samples were locally analyzed for hemoglobin concentrations, white-cell count, platelet count, prothrombin time, creatinine, glucose, hemoglobin A10 if necessary, triglycerides, cholesterol, HDL cholesterol, and LDL cholesterol. Biochemical markers of myocardial damage were analyzed at entry, after new episodes of severe chest pain, and before and 4-24 h after revascularization. The most frequently used marker of myocardial damage was CK-MB mass, but some centers used catalytic activity of total-CK, CK-B, or both. Quantitative determination of troponin-T was available in most hospitals. For screening purposes we provided all centers with a qualitative test for troponin-T, the second-generation Cardiac-T (Roche-Boehringer Mannheim, Mannheim, Germany). At randomization, blood samples from all patients were taken and stored frozen at −70° C. for central analysis of troponin-T and other markers. Conventional 12-lead electrocardiography was done on admission, at randomization, within 24 h before invasive procedures, at hospital discharge, at 3-month and 6-month outpatient visits, and on any suspicion of recurrent unstable angina or myocardial infarction. Patients in the non-invasive group who had no contraindications did a symptom-limited bicycle exercise test 16 before discharge. Echocardiography with a standard assessment of left-ventricular function was done in 1951 patients before discharge and always before invasive procedures. All exercise-test results and echocardiograms were sent to a central laboratory for assessment.

The primary objective was to compare the effects of invasive and non-invasive strategy on the composite endpoint of death and myocardial infarction after 6 months. Other predefined endpoints were total death, myocardial infarction, symptoms of angina, need for late coronary angiography and revascularization, bleeding episodes, and stroke. Myocardial infarction was defined by the occurrence of two of the three conventional criteria—typical chest pain, diagnostic electrocardiography recording (mainly new Q-wave), or a raised biochemical marker of myocardial damage according to the following definitions. For non-procedure-related myocardial infarction: concentration of CK-MB mass higher than the local hospital's diagnostic limit for myocardial infarction at one measurement; catalytic activity of CK, CK-B, or CK-MB higher than the local limit at two subsequent measurements; catalytic activity of CK, CK-B, or CK-MB higher than the double local limit at one measurement. For myocardial infarction in relation to percutaneous coronary interventions: CK-MB mass 1.5 times the local hospital's diagnostic limit for myocardial infarction at one measurement; catalytic activity of CK, CK-B, or CK-MB at one measurement three times higher than the limit; or at two measurements 1.5 times the local limit. Only new Q waves were used for the diagnosis of myocardial infarction in association with coronary-artery bypass surgery. Causes of death should be established by necropsy. All reported deaths, myocardial infarctions, raised biochemical markers in relation to percutaneous coronary interventions, and new Q waves on electrocardiography reported by the core laboratory were adjudicated by an independent clinical-event committee. Quality of data was ensured by continuous source-data verification of all case-record forms by external monitors employed by the sponsoring pharmaceutical company. All cardiac events (efficacy endpoints) and adverse-event data were continuously sent directly from the centers to the data and safety monitoring board. The study complied with the Declaration of Helsinki, and all local ethics committees approved the protocol.

Serum or plasma GDF-15 concentrations were determined on admission using the same Immunoradiometric Assay (IRMA) described in the GUSTO IV study (see Example 1, above). The differences in proportions in outcome events (myocardial infarction at 2 years, death at 2 years, myocardial infarction and death at 2 years) in tertiles of GDF-15 levels (<1200 pg/mL; 1200-1800 pg/mL; >1800 pg/mL) were recorded in the group assigned to the invasive treatment strategy and in the group assigned to the non-invasive treatment strategy. The Kaplan-Meier method was used to illustrate the timing of events during follow-up in relation to tertiles of GDF-15 in both groups (FIG. 1).

The following Table 1 shows the risks for mortality (death) and/or a further acute myocardial infarction (AMI).

TABLE 1

2-years' outcome in relation to an invasive versus a noninvasive strategy in 1045 invasive patients and 1034 non-invasive patients with NSTE-ACS enrolled in the FRISC II trial

|  | Tertiles of GDF-15 | Non-invasive % Events (Total N) | Invasive % Events (Total N) | Estimated Odds Ratio (95% CI) | p-Value |
|---|---|---|---|---|---|
| Death/AMI | <1200 | 9.3 (400) | 9.6 (416) | 1.044 (0.652 to 1.669) | 0.8584 |
|  | 1200-1800 | 16.5 (394) | 11.2 (376) | 0.637 (0.420 to 0.966) | 0.0337 |
|  | >1800 | 27.9 (240) | 14.6 (253) | 0.442 (0.282 to 0.693) | 0.0004 |
| AMI | <1200 | 8.0 (400) | 8.2 (416) | 1.024 (0.619 to 1.693) | 0.9278 |
|  | 1200-1800 | 12.9 (394) | 9.8 (376) | 0.734 (0.468 to 1.150) | 0.1772 |
|  | >1800 | 21.7 (240) | 9.5 (253) | 0.379 (0.225 to 0.638) | 0.0003 |
| Death | <1200 | 1.8 (400) | 1.4 (416) | 0.822 (0.274 to 2.466) | 0.7261 |
|  | 1200-1800 | 4.1 (394) | 2.1 (376) | 0.514 (0.217 to 1.215) | 0.1292 |
|  | >1800 | 13.3 (240) | 6.3 (253) | 0.439 (0.234 to 0.823) | 0.0102 |

Example 3

Analysis of the Patients with NSTE-ACS from the GUSTO-IV Study for Short and Long Term Mortality and Myocardial Reinfarction The investigated samples were from patients of the GUSTO-IV trial in NSTE-ACS patients performed between 1999 and 2000. The detailed design and main results of the trial have been published (Simoons 2001, Lancet 98:351-360; Ottervanger 2003, Circulation, 107: 437-442) Eligible patients were at least 21 years, with one or more episodes of angina lasting at least 5 minutes, within 24 hours of admission, and either a positive cardiac troponin tester at least 0.5 mm of ST-segment depression. Patients were randomly assigned to abciximab or placebo infusion for 24 hours or 48 hours in addition to standard medical treatment. During 30 days of follow-up, all-cause mortality and the rate of adjudicated myocardial infarctions were recorded. At 1-year follow-up, only all-cause mortality information was collected.

In a substudy of 399 consecutive patients recruited at Swedish sites, serial plasma samples were available on admission (i.e., at baseline), and at 24 hours, 48 hours, and 72 hours, which were the first to be analyzed in the present study. Based on the significant results in this cohort, it was decided to analyze GDF-15 levels in serum samples taken on admission from another 1682 random patients in the trial to obtain at least 2000 patients, and to be able to investigate the interactions with other prognostic biomarkers, i.e., troponin T, NT-proBNP, CRP, and creatinine clearance.

Plasma samples were also obtained from apparently healthy subjects included in the SWedish women and men and ISCHemic heart disease (SWISCH) study. This population consisted of 429 elderly individuals that were matched for age and gender with another contemporary NSTE-ACS population included in the FRagmin and fast revascularization during InStability in Coronary artery disease (FRISC) II trial. The detailed design and some biomarker results of the SWISCH trial have been published. Subjects with an abnormal resting 12-lead ECG, cardiovascular medication, established cardiovascular disease, other chronic disease, or acute illness were excluded from the control population. All SWISCH participants were required to demonstrate normal levels of creatinine, blood glucose, and hemoglobin, and normal white blood cell and platelet counts.

Figure 2:
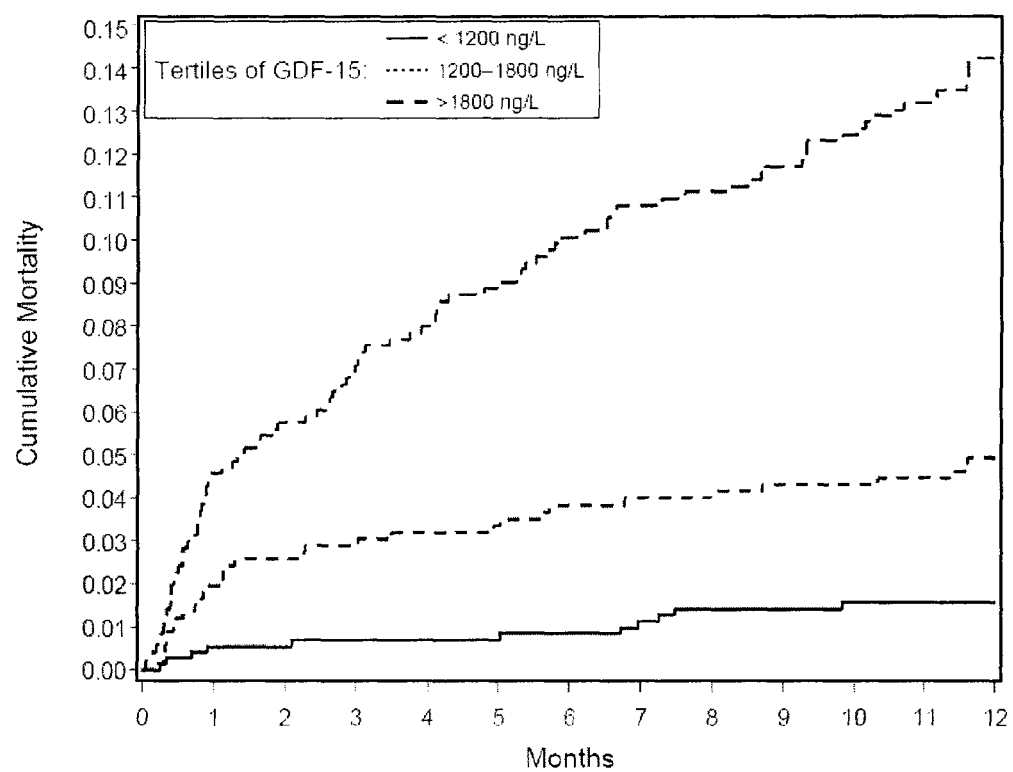
FIG. 2: Cumulative probability of death during 1 year according to tertiles of GDF-15 levels on admission in 2081 patients with NSTE-ACS enrolled in the GUSTO-IV trial (P<0.001 by log rank test).
Figure 3:
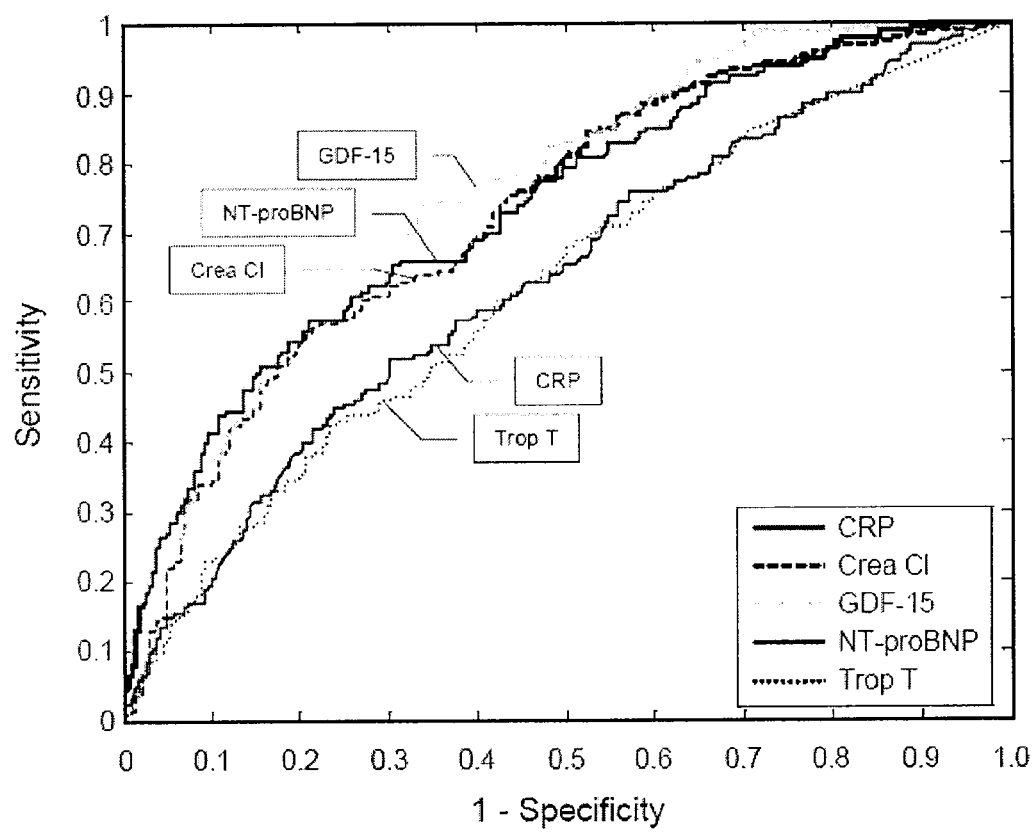
FIG. 3: Receiver operating characteristic (ROC) curve analyses relating biomarker levels to 1-year mortality in 2081 patients with NSTE-ACS enrolled in the GUSTO-IV trial. The calculated areas under the curves were 0.757 for GDF-15, 0.735 for NT-proBNP, 0.728 for creatinine clearance, 0.629 for CRP, and 0.620 for troponin T.

Baseline characteristics are presented as numbers and proportions. Continuous data are given as median and interquartile ranges. Comparisons of continuous variables between cases and controls were evaluated by non-parametric Mann-Whitney U-tests. To evaluate the relations between the levels of GDF-15 and baseline characteristics, and the levels bf troponin T, NT-proBNP, CRP, and creatinine clearance, within tertiles of GDF-15, both Spearman's rank-correlation coefficients between GDF-15 level and these factors and the Cochran-Armitage trend test for relations between proportions in several groups were used. Spearman's correlation coefficients and the Wilcoxon signed rank test were used to compare the changes of GDF-15 within the patient group over time. The differences in proportions in outcome events (myocardial infarction at 30 days, death at 30 days, myocardial infarction and death at 30 days, death at 1 year) in tertiles of GDF-15 levels were judged by the Cochran-Armitage trend test. The Kaplan-Meier method was used to illustrate the timing of events during follow-up in relation to tertiles of GDF-15 and statistical assessment was performed using the log-rank test (FIG. 2). Simple logistic regression analyses were used to identify predictors of death at 1 year. All variables were then tested in a multiple logistic regression analysis. For additional comparison of the prognostic values of GDF-15, troponin T, NT-proBNP, CRT, and creatinine clearance concerning death at 1 year, receiver operating characteristic (ROC) curves were generated, and the areas under the curves were calculated (FIG. 3). All data analyses were performed using the SAS 9.0 statistical program.

GDF-15 Levels in Apparently Healthy Control Subjects

The controls consisted of 288 men (67.1%) and 141 women (32.9%) with a median age of 65 years (interquartile range, 59 to 71 years) out of whom 14.5% were current smokers. The median GDF-15 level in this population was 762 pg/ml, with 460 762 pg/ml and 1191 pg/ml as the 10th and 90th percentiles, respectively. The upper limit of normal (ULN) was therefore rounded to 1200 pg/ml. The median (interquartile range) levels of NT-proBNP, CRP, and creatinine clearance were 74 (46 to 113) pg/ml, 1.40 (0.79 to 2.40) μg/ml, and 73 (62 to 86) ml/min, respectively. GDF-15 levels were positively correlated to age Spearman's rho=0.21; P<0.001) and inflammatory activity (CRP, rho=0.18; P<0.001), and inversely correlated to creatinine clearance (rho=0.14; P=0.002). There were no significant correlations to gender, current smoking, or NT-proBNP in this group.

GDF-15 Levels on Admission in NSTE-ACS Patients

The NSTE-ACS patients consisted of 1315 men (63.2%) and 766 women (36.8%), with a median age of 66 years (interquartile range 57 to 74 years). Although the patients were slightly older than the healthy controls (P=0.014), the two cohorts were well comparable concerning age and gender. There was no influence of the randomized abciximab treatment on GDF-15 levels measured at any time point, and therefore, the randomized groups were combined. The time from symptom onset to admission, the prevalence of cardiovascular risk factors, previous manifestations of and treatments for cardiovascular disease, and ECG signs of ongoing ischemia, and the baseline levels of troponin T, NT-proBNP, CRP, and creatinine clearance in this patient population are presented in Table 2. The NSTE-ACS patients displayed significantly (P<0.001) higher GDF-15 levels compared to the healthy controls; the median was 1445 pg/ml, and 850 pg/ml, 1187 pg/ml, 1817 pg/ml, and 3314 pg/ml marked the 10th, 33rd, 66th, and 90th percentiles, respectively. Accordingly, about two thirds of the NSTE-ACS patients had GDF-15 levels above the ULN (90th percentile) in healthy controls. As this ULN corresponded to the lower tertile in patients, the patient material was stratified in tertiles (cut off limits 1200 and 1800 pg/ml) when related to outcome.

Relation between GDF-15 Levels and Clinical and Biochemical Factors in NSTE-ACS

Increasing tertiles of GDF-15 on admission were positively associated with age, female gender, history of hypertension and diabetes, previous manifestations of cardiac disease, i.e., angina pectoris, myocardial infarction, coronary revascularization, and heart failure, ACE inhibitor therapy, and also with markers of ongoing ischemia and necrosis, myocardial dysfunction, and inflammation, as indicated by ST-segment depression, and the levels of troponin T, NT-proBNP, and CRP (Table 2); GDF-15 levels were inversely related to current smoking and creatinine clearance (Table 2). In a multiple regression analysis using the natural logarithm of GDF-15 as the dependent variable, the following factors were significantly associated with GDF-15: age (P<0.001), male gender (P<0.001), time from symptom onset to admission (P=0.006; inverse relation), current smoking (P<0.001), diabetes (P<0.001), history of heart failure (P<0.001), ST-segment depression (P=0.050), NT-proBNP (P<0.001), CRP (P<0.001), and creatinine clearance (P<0.001; inverse relation). There was no independent relation to the level of troponin T (P=0.436).

TABLE 2

Characteristics of NSTE-ACS Patients According to Tertiles of GDF-15 Levels on Admission

| | Derivation Study (n = 235) | Validation Study (n = 220) | P Value |
|---|---|---|---|
| Clinical characteristics | | | |
| Age [years] | 66 (56-72) | 63 (58-69) | 0.161 |
| Male gender | 215 (91.5) | 197 (89.5) | 0.479 |
| BMI [kg/m$^2$]$^a$ | 25.4 (23.0-29.3) | 26.1 (23.7-28.7) | 0.444 |
| Ischemic etiology | 168 (71.5) | 146 (63.6) | 0.085 |

TABLE 2-continued

Characteristics of NSTE-ACS Patients According
to Tertiles of GDF-15 Levels on Admission

|  | Derivation Study (n = 235) | Validation Study (n = 220) | P Value |
|---|---|---|---|
| Heart failure severity and biomarkers | | | |
| NYHA class | 2.7 ± 0.8 | 2.2 ± 0.7 | <0.001 |
| I | 12 (5.1) | 31 (14.1) | |
| II | 84 (35.7) | 111 (50.5) | |
| III | 96 (40.9) | 72 (32.7) | |
| IV | 43 (18.3) | 6 (2.7) | |
| LVEF [%] | 30 (24-40) | 33 (27-38) | 0.082 |
| Creatinine [μmol/L] | 102 (84-137) | 99 (90-115) | 0.430 |
| Crea clearance [mL/min][a] | 71.5 (45.6-90.8) | 68.4 (53.8-88.8) | 0.638 |
| Uric acid [μmol/L][b] | 422 (345-529) | 390 (330-450) | 0.392 |
| Hemoglobin [g/dL][c] | 13.8 (12.3-14.9) | 14.0 (13.1-14.8) | 0.108 |
| NT-proBNP [ng/L] | 1340 (434-3740) | 521 (209-1070) | <0.001 |
| GDF-15 [ng/L] | 2240 (1232-4010) | 1465 (1004-2194) | <0.001 |
| Medication at baseline | | | |
| ACE inhibitor or ARB | 183 (77.9) | 213 (96.8) | 0.004 |
| β-Blocker | 112 (47.7) | 146 (66.4) | <0.001 |
| Diuretic | 167 (71.1) | 194 (88.2) | <0.001 |
| Spironolactone | 58 (24.7) | 50 (22.7) | 0.703 |

Values are n (%), median (25th and 75th percentiles), or mean ± SD.
[a]Data available from 216 patients in the derivation cohort and 198 patients from the validation cohort;
[b]data from 207 patients in the validation cohort;
[c]data from 214 patients in the validation cohort.
BMI denotes body mass index; LVEF, left ventricular ejection fraction; ARB, angiotensin receptor blocker.

Temporal Evolution of GDF-1 S Levels in NSTE-ACS

The temporal evolution of GDF-15 serum levels during an episode of unstable coronary artery disease was studied in a cohort of 399 patients in the NSTE-AGS population in whom samples were available on admission, and after 24 hours, 48 hours, and 72 hours. Linear regression analysis of the natural logarithm of GDF-15 versus lime revealed a weak but statistically significant (P=0.010) slope, indicating that there was a gradual increase during this time interval. However, as shown in Table 3, GDF-15 levels at these four time points stayed within the same range. There was a very limited intra-individual variation over time, as shown by the close correlation between the GDF-15 levels on admission and at later time points (Table 3). Accordingly, 67.4%, 69.7%, and 70.4% of the patients had GDF-15 levels above the ULN at 24 hours, 48 hours, and 72 hours, respectively.

TABLE 3

Temporal Evolution of GDF-15 Levels in NSTE-ACS Patients

| | | Follow-up | | |
|---|---|---|---|---|
| | Baseline | 24 hours | 48 hours | 72 hours |
| GDF-15 (ng/L) | | | | |
| Median | 1499 | 1575 | 1630 | 1664 |
| Interquartile range | (1151 to 2203) | (1112 to 2286) | (1163 to 2396) | (1140 to 2357) |
| Spearman's correlation coefficients (follow-up vs. baseline) | — | 0.89 | 0.80 | 0.72 |
| | | P < 0.001 | P < 0.001 | P < 0.001 |
| Change in GDF-15 level (follow-up vs. baseline, ng/L) | | | | |
| Median | — | 48 | 74 | 124 |
| Interquartile range | | (−111 to 253) | (−146 to 360) | (−143 to 434) |
| | | P = 0.001 | P < 0.001 | P < 0.001 |

In a cohort of 399 patients, GDF-15 levels were determined on admission (baseline), and after 24 hours, 48 hours, and after 72 hours. Spearman's correlation coefficients and P values were calculated to describe the relations between GDF-15 levels at follow-up and baseline. Changes in GDF-15 levels at follow-up compared to baseline were assessed by the Wilcoxon signed rank test.

GDF-15 Levels and Mortality in NSTE-ACS

The risk of death in patients with NSTE-ACS during follow-up increased markedly with increasing levels of GDF-15 on admission (FIG. 2). The Kaplan-Meier mortality curves for the different tertiles showed an early separation, with 30-day mortality rates of 0.6%, 2.0%, and 4.3%, respectively (P<0.001). Separation of the curves continued throughput the first year after the index event, and after 1 year of follow-up, mortality rates were 1.5%, 5.0%, and 14.1% in the respective tertiles (P<0.001). ROC analyses further illustrated that GDF-15 is a strong biochemical indicator of mortality with an area under the curve (AUC) of 0.757, as compared to NT-proBNP (AUC=0.735), creatinine clearance (AUC=0.728), CRP (AUC=0.629), and troponin T (AUC=0.620) (FIG. 3). By simple logistic regression analysis, age, history of hypertension, diabetes, previous angina pectoris or myocardial infarction, history of congestive heart failure, and the levels of troponin T, NT-proBNP, CRP, creatinine clearance, and GDF-15 were all related to 1-year mortality (Table 4). Using a multiple logistic regression approach, age, previous myocardial infarction, and increased levels of NT-proBNP and GDF-15 emerged as the only independent predictors (Table 4). Among these independent risk indicators, the GDF-15 level emerged as the strongest predictor of mortality (Table 4). The results were unchanged when using a backward stepwise approach or stratification of GDF-15 levels and the other biomarkers in tertiles. Also when added one at a time in stepwise selection, the only variables left significant were age, previous myocardial infarction, NT-proBNP and GDF-15. Notably, GDF-15 levels measured on admission or at later time points in the cohort of 399 patients provided similar prognostic information on 1-year mortality although it seemed that the GDF-15 levels within the initial 24 hours had the highest predictive value (Table 5).

these markers were therefore combined and used on top of the independent clinical predictor of mortality, previous myocardial infarction. The results illustrate that a combination of increasing tertiles of GDF-15 and NT-proBNP levels pro-

TABLE 4

Logistic Regression Analyses for 1-Year Mortality in 2081 Patients with NSTE-ACS in Relation to Baseline Characteristics, Medical History, and Measurements on Admission

|  | Univariate model | | Multivariate model | |
| --- | --- | --- | --- | --- |
|  | Estimated odds ratio (95% CI) | P Value | Estimated odds ratio (95% CI) | P Value |
| Age (per year) | 1.087 (1.066 to 1.108) | <0.001 | 1.044 (1.013 to 1.077) | 0.006 |
| Gender (male vs. female) | 0.723 (0.513 to 1.018) | 0.064 | 1.134 (0.730 to 1.764) | 0.574 |
| Time from symptoms (per hour) | 0.995 (0.971 to 1.020) | 0.695 | 0.980 (0.951 to 1.010) | 0.185 |
| Current smoking [1] | 0.727 (0.466 to 1.135) | 0.161 | 1.674 (0.930 to 3.012) | 0.086 |
| History of hypertension [1] | 1.796 (1.265 to 2.550) | 0.001 | 1.102 (0.715 to 1.699) | 0.658 |
| History of hypercholesterolemia [1] | 1.016 (0.692 to 1.490) | 0.936 | 1.386 (0.876 to 2.192) | 0.163 |
| Diabetes mellitus [1] | 2.251 (1.564 to 3.240) | <0.001 | 1.396 (0.883 to 2.207) | 0.153 |
| Previous angina pectoris [1] | 1.727 (1.221 to 2.445) | 0.002 | 1.075 (0.694 to 1.664) | 0.746 |
| Previous myocardial infarction [1] | 2.945 (2.087 to 4.156) | <0.001 | 1.904 (1.224 to 2.963) | 0.004 |
| Previous Revascularization [1] | 0.746 (0.437 to 1.273) | 0.283 | 0.583 (0.311 to 1.093) | 0.092 |
| History of heart failure [1] | 3.404 (2.124 to 5.454) | <0.001 | 1.161 (0.647 to 2.084) | 0.617 |
| ST-segment depression ≥0.5 mm [1] | 1.348 (0.851 to 2.134) | 0.203 | 1.068 (0.603 to 1.889) | 0.822 |
| Troponin T [2] | 1.255 (1.141 to 1.381) | <0.001 | 1.085 (0.948 to 1.241) | 0.236 |
| NT-proBNP [2] | 1.902 (1.674 to 2.161) | <0.001 | 1.296 (1.063 to 1.580) | 0.010 |
| CRP [2] | 1.453 (1.278 to 1.654) | <0.001 | 1.045 (0.888 to 1.230) | 0.596 |
| Creatinine clearance [3] | 0.962 (0.954 to 0.971) | <0.001 | 0.995 (0.982 to 1.009) | 0.494 |
| GDF-15 [2] | 4.817 (3.625 to 6.402) | <0.001 | 2.197 (1.431 to 3.371) | <0.001 |

[1] For yes;
[2] for one unit in the natural logarithms scale as the variables troponin T, NT-proBNP, CRP, and GDF-15 were transformed to their natural logarithms before analysis;
[3] for 1 mL/min change.

TABLE 5

GDF-Tertiles at Baseline and Follow-up as Predictors of 1-Year Mortality

|  | 1-Year mortality according to GDF-15 levels at | | | |
| --- | --- | --- | --- | --- |
|  | Baseline | 24 hours | 48 hours | 72 hours |
| GDF-15 <1200 ng/L | 1 (0.8) | 3 (2.5) | 3 (2.7) | 5 (4.5) |
| GDF-15 1200-1800 ng/L | 3 (2.4) | 0 (0) | 5 (4.3) | 2 (1.7) |
| GDF-15 >1800 ng/L | 19 (12.7) | 20 (12.1) | 15 (8.7) | 16 (9.5) |
| P Value* | <0.001 | <0.001 | 0.037 | 0.051 |

In a cohort of 399 patients, GDF-15 levels were determined on admission (baseline), and after 24 hours, 48 hours, and after 72 hours. At each time point, patients were stratified in tertiles according to their GDF-15 levels. The number (%) of deaths at 1 year according to GDF-15 tertiles are presented.
*Cochran-Armitage trend test.

GDF-15 Levels and the Risk of Recurrent Myocardial Infarction in NSTE-ACS

The GDF-15 level on admission was also strongly related to the risk of the composite end-point of death or recurrent myocardial infarction at 30 days. With rising tertiles of GDF-15, the risk of death or myocardial infarction at 30 days was 5.0, 6.9, and 10.8%, respectively (P<0.001). This relationship was mainly driven by the association of GDF-15 with mortality. Although, the risk of a subsequent myocardial infarction within 30 days after the index event was significantly related to increasing tertiles of GDF-15, with rates of 4.8, 5.6, and 7.2%, respectively (P=0.048), there was no independent relation between GDF-15 and the rate of recurrent myocardial infarction at 30 days by multiple logistic regression analysis.

Combination of GDF-15 with Markers of Prognosis in NSTE-ACS

Figure 4:
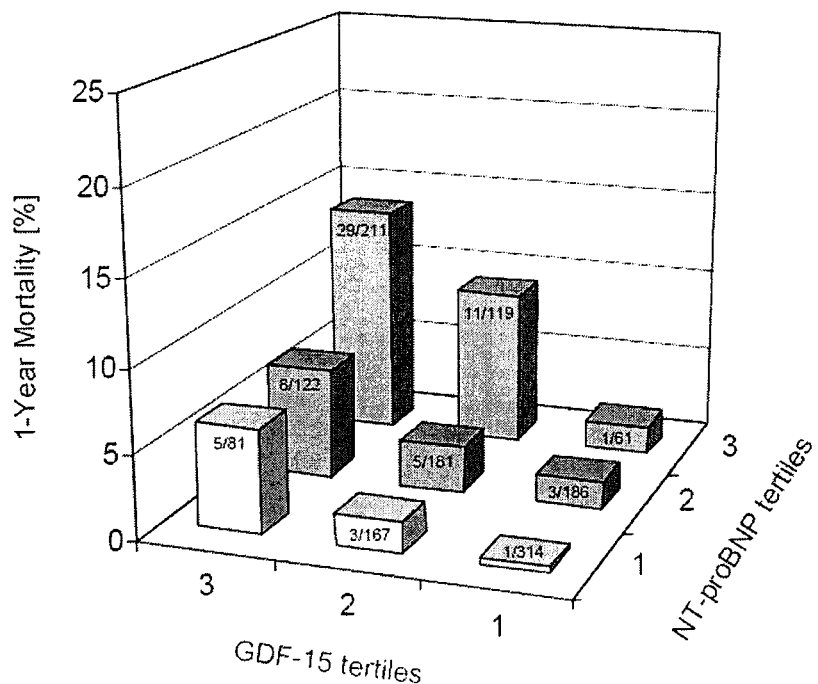
FIGS. 4A-B illustrate mortality at 1-year follow-up among strata of patients with NSTE-ACS enrolled in the GUSTO-IV trial (A) without a history of previous myocardial infarction with the number of deaths per number of patients shown for each column, and (B) with a history of a previous myocardial infarction, according to tertiles of GDF-15 and NT-proBNP levels on admission, with the number of deaths per number of patients shown for each column.
Figure 4:
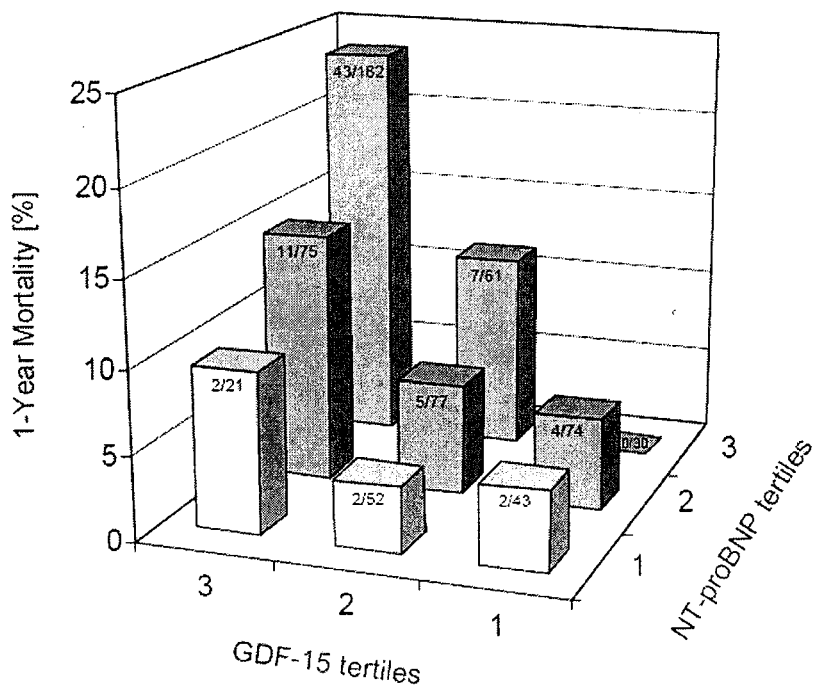

The multiple logistic regression analyses showed that GDF-15 and NT-proBNP were the only biomarkers with an independent prognostic importance for mortality. Tertiles of these markers were therefore combined and used on top of the independent clinical predictor of mortality, previous myocardial infarction. The results illustrate that a combination of increasing tertiles of GDF-15 and NT-proBNP levels provided additive prognostic information, and identified strata of patients with a 1-year mortality rate ranging from 0.3 to 13.7% in patients without a history of a previous myocardial infarction, and from 4.7 to 23.6% in patients with a previous myocardial infarction (FIG. 4). These relationships were further modified only by the age of the patient, with a 4.4% relative change in mortality risk for every one year of age (Table 4).

Example 3

Prognostic Utility of GDF-15 in Patients with Chronic Heart Failure

The relation of GDF-15 levels to clinical and biochemical baseline parameters and survival in a cohort of 235 patients with CHF enrolled at four European centers in Athens (Greece, n=51), London (United Kingdom, n=89), and Wroclaw/Zabre (Poland, n=95) (derivation cohort) was initially investigated. In the validation cohort, we prospectively evaluated the principle hypothesis from the derivation cohort, i.e., that increased circulating levels of GDF-15 provide independent prognostic information in patients with CHF. The validation cohort included 220 patients with CHF who were recruited in Verona (Italy). All patients participated in projects designed to investigate novel neurohormonal and inflammatory prognostic biomarkers in chronic heart failure and provided written informed consent. In all patients, the diagnosis of CHF was based on symptoms and clinical signs, and evidence of left ventricular enlargement or systolic functional impairment by radionuclide or invasive ventriculography, or echocardiography. All patients had a history of CHF for at least six months and were stable on medication for at least four weeks prior to the study. Patients with myocardial infarction within the past 12 weeks, known inflammatory or malignant disease, or creatinine levels >400 µmol/L were excluded. The institutional ethics committees of all participating study sites approved the protocol.

Patients were followed by outpatient assessments and telephone contact. Survival status was censored on May 25, 2005 in the derivation cohort and on May 31, 2006 in the validation cohort. No patient was lost to follow-up. The primary end point of the study was all-cause mortality. In the validation cohort, information on the cause of death was also available. Nine patients undergoing heart transplantation were censored alive at the time of the event.

Venous blood samples were drawn after ≥10 minutes of rest in a semi-recumbent position for assessment of GDF-15 and other parameters. GDF-15 concentrations were determined by an immunoradiometric assay (IRMA) using a polyclonal, GDF-15 affinity chromatography-purified, goat anti-human GDF-15 IgG antibody from R&D Systems (AF957), as recently described. All GDF-15 measurements were performed at Hannover Medical School by investigators that were not aware of patients' characteristics and outcomes. NT-proBNP levels were determined by a chemiluminescence immunoassay (ELICIA, Roche Diagnostics). Creatinine, uric acid, and hemoglobin measurements were performed at the participating study centers. Creatinine clearance was calculated according to the Cockcroft and Gault equation.

Baseline characteristics are expressed as median (25th and 75th percentiles), mean±standard deviation, or absolute numbers and percentages, as appropriate. The Kolmogorov-Smirnov test was used to test for a normal distribution of continuous variables. Continuous variables were compared by Mann-Withney test or unpaired Student's t-test. Comparisons between strata of patients were performed by Kruskal-Wallis test or ANOVA. Proportions were compared by using the chi-square test. Multiple regression analyses were applied to identify factors that were independently associated with GDF-15 levels. Univariate and multivariate Cox proportional hazards analyses were employed to assess prognostic associations. Kaplan-Meier plots were used to illustrate the timing of events during follow-up in relation to GDF-15 levels and statistical assessment was performed by Cox regression analysis. For additional comparison of the prognostic values of GDF-15, creatinine, uric acid, hemoglobin, and NT-proBNP, receiver operating characteristic (ROC) curves were generated, and the areas under the curves (AUCs) were calculated. All data analyses were performed using either StatView 5.0.1 or MedCalc 8.2.0.3 (ROC analyses) statistical programs.

Figure 5A:
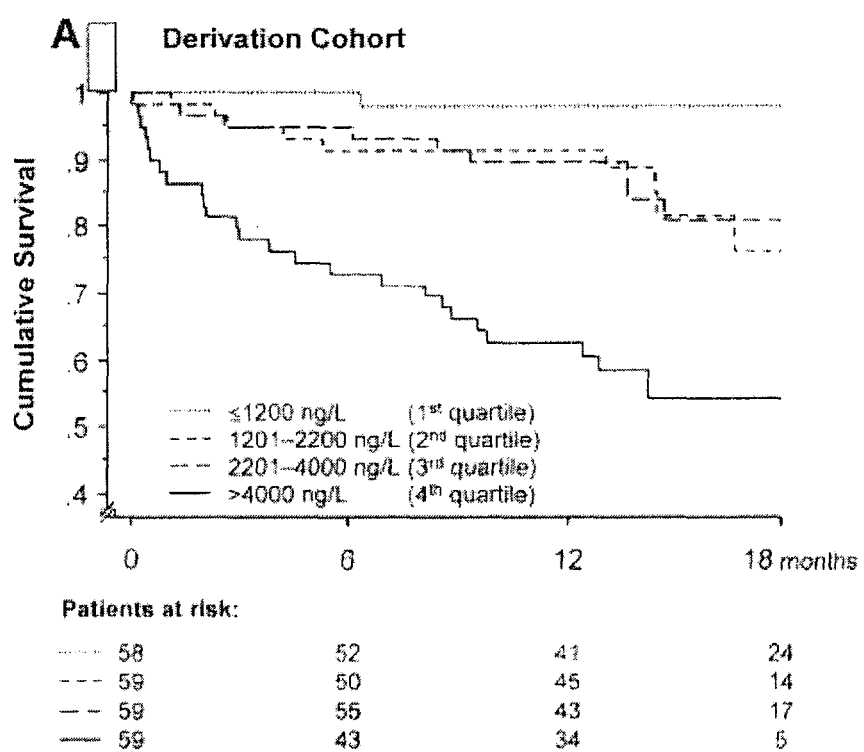
FIGS. 5 A-B illustrate cumulative survival in patients with chronic heart failure from (A) the derivation cohort according to quartiles of GDF-15 (P, 0.001 by log-rank test), and (B) from the validation cohort; patients were stratified according to the cut-off levels defined in the derivation cohort (P, 0.001 by log-rank test). The number of patients at risk is shown at the bottom.

The derivation cohort consisted of 235 patients with a median age of 66 years (25th and 75th percentiles, 56-72). The clinical and biochemical characteristics of the patients are summarized in Table 6. The median GDF-15 level was 2240 (1232-4010) ng/L. Approximately three quarters of the patients (75.3%) presented with GDF-15 levels above 1200 ng/L, the upper limit of normal (ULN) in apparently healthy elderly subjects. GDF-15 levels were closely related to NYHA functional class: NYHA I: 850 (646-1747) ng/L, NYHA II: 1621 (1025-2563) ng/L, NYHA III: 2510 (1385-3686) ng/L, NYHA IV: 4869 (2722-8807) ng/L (P<0.001 for trend). As the ULN corresponded to the lower quartile boundary in the derivation cohort, patients were stratified in quartiles (cut-off limits, 1200, 2200, and 4000 ng/L) for further analyses. Out of 235 patients in the derivation cohort, 68 (28.9%) died during follow-up. The 12- and 18-month mortality rates were 15.0% (95% CI, 10.3-19.7) and 22.9% (95% CI, 16.5-29.3), respectively. The risk of death during follow-up increased markedly with increasing quartiles of GDF-15 (FIG. 5A). The mortality rates were 2.0, 8.7, 10.5, and 37.5% at 12 months, and 2.0, 23.8, 19.1, and 45.6% at 18 months in the respective quartiles (P<0.001).

The validation cohort consisted of 220 patients with a median age of 63 (58-69) years. Patients in the validation cohort were less symptomatic (NYHA class), presented with lower NT-proBNP levels, and were treated more often with ACE inhibitors or angiotensin receptor blockers, β-blockers, or diuretics, but had similar age, gender distribution, body mass index, heart failure etiology, LVEF, renal function, uric acid and hemoglobin levels as compared to the derivation cohort (Table 6). The median GDF-15 level was 1465 (1004-2194) ng/L, which was significantly lower than in the derivation cohort (Table 6); 60.5% of the patients in the validation cohort presented with GDF-15 levels above the ULN. GDF-15 levels were closely related to NYHA functional class in the validation cohort: NYHA I: 1106 (849-1682) ng/L, NYHA II: 1294 (1007-1945) ng/L, NYHA III: 1903 (1122-2650) ng/L, NYHA IV: 4147 (1971-5905) ng/L (P<0.001 for trend).

TABLE 6

Patients' Characteristics

| | Derivation Study (n = 235) | Validation Study (n = 220) | P Value |
|---|---|---|---|
| Clinical characteristics | | | |
| Age [years] | 66 (56-72) | 63 (58-69) | 0.161 |
| Male gender | 215 (91.5) | 197 (89.5) | 0.479 |
| BMI [kg/m$^2$]$^a$ | 25.4 (23.0-29.3) | 26.1 (23.7-28.7) | 0.444 |
| Ischemic etiology | 168 (71.5) | 140 (63.6) | 0.085 |
| Heart failure severity and biomarkers | | | |
| NYHA class | 2.7 ± 0.8 | 2.2 ± 0.7 | <0.001 |
| I | 12 (5.1) | 31 (14.1) | |
| II | 84 (35.7) | 111 (50.5) | |
| III | 96 (40.9) | 72 (32.7) | |
| IV | 43 (18.3) | 6 (2.7) | |
| LVEF [%] | 30 (24-40) | 33 (27-38) | 0.082 |
| Creatinine [µmol/L] | 102 (84-137) | 99 (90-115) | 0.430 |
| Crea clearance [mL/min]$^a$ | 71.5 (45.6-90.8) | 68.4 (53.8-88.8) | 0.638 |
| Hemoglobin [g/dL]$^c$ | 13.8 (12.3-14.9) | 14.0 (13.1-14.8) | 0.108 |
| NT-proBNP [ng/L] | 1340 (434-3740) | 521 (209-1070) | <0.001 |
| GDF-15 [ng/L] | 2240 (1232-4010) | 1465 (1004-2194) | <0.001 |
| Medication baseline | | | |
| ACE inhibitors or ARBs | 183 (77.9) | 213 (96.8) | 0.004 |
| β-Blockers | 112 (47.7) | 146 (66.4) | <0.001 |
| Diuretics | 167 (71.1) | 194 (88.2) | <0.001 |

TABLE 6-continued

| Patients' Characteristics | | | |
|---|---|---|---|
| | Derivation Study (n = 235) | Validation Study (n = 220) | P Value |
| Spironolactone | 58 (24.7) | 50 (22.7) | 0.703 |
| Uric acid [μmol/L][b] | 422 (345-529) | 390 (330-450) | 0.392 |

Values are n (%), median (25th and 75th percentiles), or mean ± SD.
[a]Data available from 216 patients in the derivation cohort and 198 patients from the validation cohort;
[b]data from 207 patients in the validation cohort;
[c]data from 214 patients in the validation cohort.
BMI denotes body mass index; LVEF, left ventricular ejection fraction; ARB, angiotensin receptor blocker.

Figure 5B:
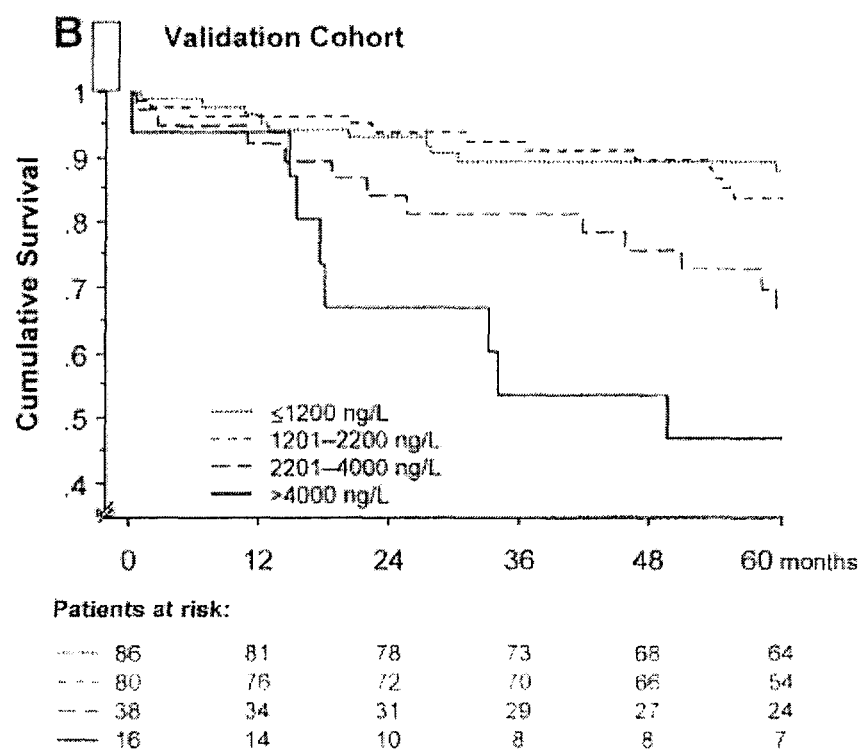

Out of 220 patients in the validation cohort, 49 (22.3%) died during follow-up. The 12-, 18-, and 60-month mortality rates were 4.6% (95% CI, 1.9-7.3), 6.9% (95% CI, 3.6-10.2), and 18.6% (95% CI, 13.3-23.9), respectively. Using the cut-off limits established in the derivation cohort, increasing levels of GDF-15 were closely related to all-cause mortality (FIG. 5B). The mortality rates were 3.5, 3.8, 8.0, and 6.3% at 12 months, 5.9, 3.8, 10.7, and 26.3% at 18 months, and 10.7, 16.2, 27.2, and 53.1% at 60 months in patients with GDF-15 levels ≤1200 ng/L, between 1201 and 2200 ng/L, between 2201 and 4000 ng/L, and >4000 ng/L, respectively (P<0.001). Both, patients who died from progressive heart failure, and patients who died suddenly had significantly higher GDF-15 levels as compared to the survivors (Table 7).

TABLE 7

Multivariate Cox Regression Analysis for All-Cause Mortality

| | Derivation Cohort | | Validation Cohort | |
|---|---|---|---|---|
| Characteristics | HR (95% CI) | P Value | HR (95% CI) | P Value |
| Age (per 10 years) | 1.158 (0.906-1.479) | 0.241 | 1.190 (0.776-1.826) | 0.425 |
| Male gender | 3.491 (0.787-15.49) | 0.100 | 1.018 (0.369-2.811) | 0.973 |
| Ischemic etiology | 1.101 (0.627-1.931) | 0.738 | 1.009 (0.525-1.939) | 0.979 |
| LVEF (per 10% decrease) | 1.609 (1.241-2.086) | <0.001 | 1.843 (1.177-2.885) | 0.008 |
| NYHA class (per class) | 1.296 (0.889-1.891) | 0.177 | 1.039 (0.640-1.688) | 0.877 |
| Ln Creatinine | 2.329 (0.939-5.781) | 0.068 | 0.523 (0.102-2.684) | 0.437 |
| Ln Uric Acid | 0.903 (0.398-2.047) | 0.806 | 0.817 (0.239-2.787) | 0.747 |
| Hb (per 1 g/dL decrease) | 1.094 (0.939-1.273) | 0.248 | 0.952 (0.758-1.197) | 0.676 |
| Ln NT-proBNP | 1.076 (0.836-1.386) | 0.569 | 1.153 (0.824-1.613) | 0.407 |
| Ln GDF-15 | 2.156 (1.307-3.566) | 0.003 | 2.888 (1.345-6.200) | 0.007 |

Hazard ratios (HR) with 95% confidence intervals (CI) and P values are shown. Creatinine, uric acid, NT-proBNP, and GDF-15 were not normally distributed and therefore transformed to their natural logarithms before analysis; hazard ratios refer to an increase of one unit in the natural logarithms scale in these variables. Hb denotes hemoglobin.

Figure 6A:
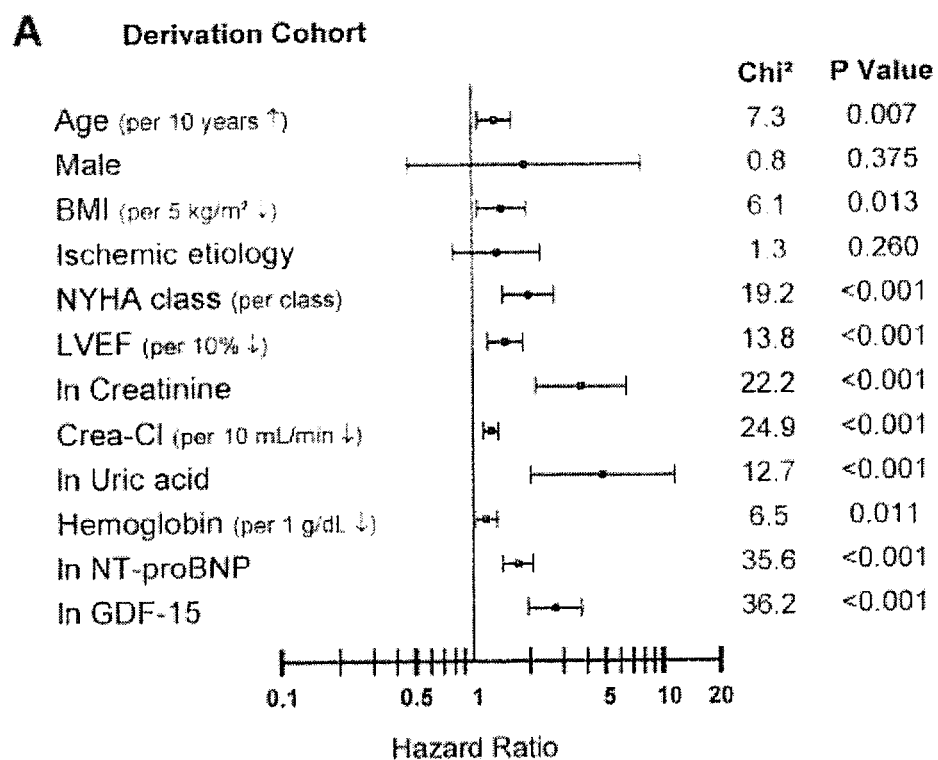
FIGS. 6A-B illustrate univariate predictors of mortality during follow-up in patients with chronic heart failure (A) from the derivation cohort, and (B) from the validation cohort. Hazard ratios with 95% confidence intervals, Chi$^2$ and P values are shown. Creatinine, uric acid, NT-proBNP, and GDF-15 were not normally distributed and therefore transformed to their natural logarithms before analysis; hazard ratios refer to an increase of one unit in the natural logarithms scale in these variables.
Figure 6B:
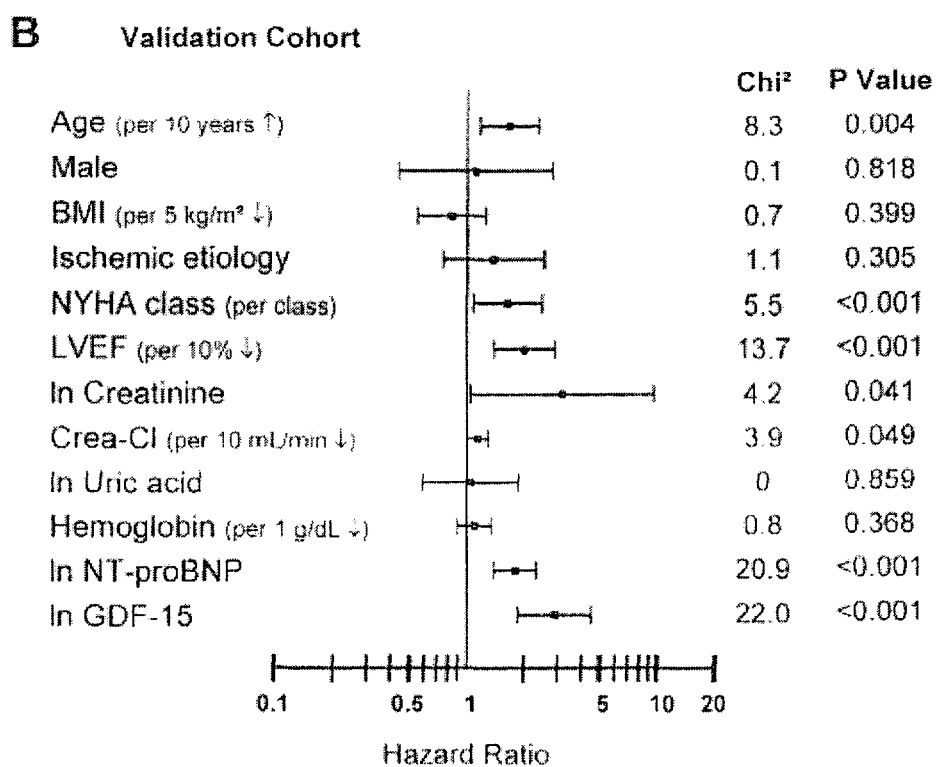

Several clinical characteristics and biochemical parameters are indicative of a poor prognosis in patients with CHF, and univariate Cox regression analyses confirmed the utility of a number of these established markers in both patient cohorts (FIG. 6, A and B). Advanced age, higher NYHA class, reduced LVEF, lower creatinine clearance, and increased levels of creatinine and NT-proBNP were associated with an increased risk of death in both cohorts. Increased levels of uric acid, reduced body mass index, and reduced hemoglobin concentrations predicted all cause mortality in the derivation cohort only. Consistent with the data shown in FIG. 5, higher levels of GDF-15 were associated with a significant increase in mortality in both cohorts. By multivariate Cox regression analysis, GDF-15 and LVEF emerged as the only independent predictors of all-cause mortality, both in the derivation and the validation cohort (Table 7). The results were unchanged with GDF-15 as a continuous variable. In the combined material, GDF-15 (P<0.001), together with LVEF (P<0.001) and age (P=0.003) emerged as independent predictors. When body mass index and creatinine clearance (data available from 408 patients) were included in the model, GDF-15 (P<0.001), together with LVEF (P<0.001) and creatinine clearance (P=0.045) independently predicted all-cause mortality. ROC curve analyses further illustrated that GDF-15 is a strong biochemical indicator of mortality with an area under the curve (AUC) of 0.830 (95% CI, 0.783-0.870), which was not significantly different (P=0.523) from the AUC of NT-proBNP (0.852; 95% CI, 0.806-0.890), but significantly (P<0.001) greater than the AUCs for creatinine (0.646; 95% CI, 0.589-0.700), uric acid (0.657; 95% CI, 0.598-0.708), and hemoglobin (0.655; 95% CI, 0.598-0.708). The best GDF-15 level for predicting mortality after 18 months in the combined patient population was 2729 ng/L (sensitivity, 81.1%; specificity, 71.2%; positive likelihood ratio, 2.81) Additional ROC curve analyses indicated that 2729 ng/L was also the best cut-off value to predict mortality after 12 months (data not shown).

Example 4

Prognostic Utility of GDF-15 in Patients with Pulmonary Embolism

Figure 7:
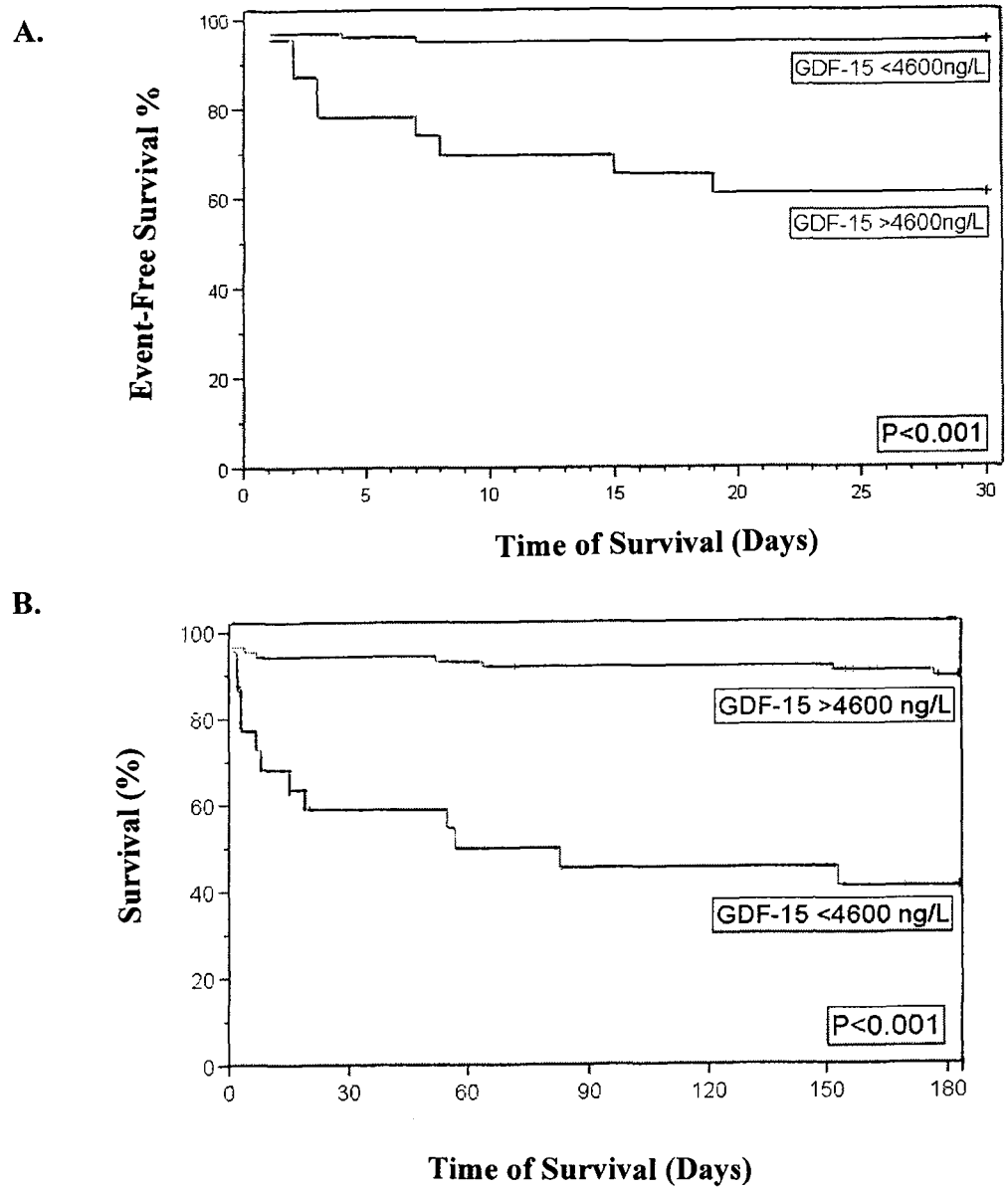
FIGS. 7A-B illustrate survival rate without adverse events of patients within a time window of (A) 30 days. and (B) 180 days. Patients have been classified according to their GDF-15 levels (above or below 4,600 ng/L).

The amount of GDF-15 has been determined in serum samples of a cohort of 123 patients suffering from acute pulmonary embolism as described in the Examples before. Patients suffering from pulmonary embolism showed significantly increased median levels for GDF-15 (2,196 pg/ml; percentiles 25-75: 1,333 to 3,457 pg/ml) in comparison to healthy individuals (p<0.001). Specifically, 82% (n=101) had GDF-15 levels higher than the upper limit of normal of 1,200 pg/ml. Patients which developed severe complications (intubation, catecholamine administration or cardiopulmonary reanimation required) or which died within 30 days upon sampling (n=17) exhibited serum levels of up to 6,039 pg/ml in the median and percentiles 25-75. of 2,778 to 19,722 pg/ml while patients which showed no complications had serum levels of 2,036 pg/ml in the median and percentiles 25-75. of 1,279 pg/ml to 3,176 pg/ml (p<0.001). Evaluation of the data showed that a GDF-15 level of more than 4,600 pg/ml indicates a 10-times increase risk of developing complications or death (i.e., the risk increased from 5.0% to 52.2%; p<0.001); see FIG. 7 (A). Within six month, the risk remained increased up to 7.7-times for death (n=22); see FIG. 7 (B).

What is claimed is:

1. A method for identifying a subject as suitably treated by a cardiac intervention, the method comprising:
   contacting a portion of a sample from the subject with an antibody having specific binding affinity for growth differentiation factor 15 (GDF-15), thereby forming a complex between the antibody and GDF-15, the antibody having a detectable label;
   separating the complex formed in said step of contacting from antibody not comprising the complex;
   quantifying a signal from the detectable label of the antibody comprising the complex formed in said step of contacting, the signal being proportional to an amount of GDF-15 in the sample, whereby an amount of GDF-15 in the sample is calculated;
   comparing the amount of GDF-15 calculated in said step of quantifying to a reference amount for GDF-15, wherein the reference amount for GDF-15 is 1200 pg/ml; and
   identifying the subject as suitably treated by a cardiac intervention if the amount of GDF-15 calculated in said step of quantifying is larger than the reference threshold amount for GDF-15.

2. The method of claim 1, wherein said cardiac intervention the subject is identified as being suitably treated thereby is selected from the group consisting of percutaneous coronary angioplasty, percutaneous transluminal coronary balloon angioplasty, laser angioplasty, coronary stent implantation, bypass implantation, and intraluminal techniques to restore blood flow, vessel patency, stabilize plaque, and reduce intracoronary thrombus load.

3. The method of claim 1 further comprising the steps of:
   determining an amount of a cardiac troponin in said sample; and
   comparing the amount of the cardiac troponin to a reference amount for the cardiac troponin,
   wherein said step of identifying comprises identifying the subject as suitably treated by cardiac intervention if the amount of GDF-15 determined in said step of determining is larger than the reference amount for GDF-15 and the amount of cardiac troponin determined in said further step of determining is larger than the reference amount for cardiac troponin.

4. The method of claim 3 wherein said cardiac troponin is troponin T.

5. The method of claim 3 further comprising steps of:
   determining an amount of a natriuretic peptide in said sample; and
   comparing the amount of the natriuretic peptide to a reference amount for the natriuretic peptide,
   wherein said step of identifying comprises identifying the subject as suitably treated by cardiac intervention if the amount of GDF-15 determined in said step of determining is larger than the reference amount for GDF-15 and the amount of cardiac troponin determined in said step of determining is larger than the reference amount for cardiac troponin and the amount of natriuretic peptide determined in said step of determining is larger than the reference amount for natriuretic peptide.

6. The method of claim 5 wherein said natriuretic peptide is NT-proBNP.

7. The method of claim 4 wherein said reference amount of cardiac troponin is 0.01 ng/ml.

8. The method of claim 6 wherein said reference amount of natriuretic peptide is 1000 pg/ml.

9. A method for determining whether a patient diagnosed with heart failure is sensitive to a cardiac intervention therapy, comprising:
   determining an amount of growth differentiation factor 15 (GDF-15) in a sample from the subject; and
   comparing the amount of GDF-15 determined to a reference amount for GDF-15 and;
   providing an identification of sensitive to a cardiac intervention therapy if the amount of GDF-15 determined in said step of determining is greater than the reference amount for GDF-15, the reference amount for GDF-15 being 1200 pg/ml.

10. The method of claim 9, wherein said therapy is a drug-based therapy.

11. The method of claim 10, wherein said drug is selected from the group consisting of an angiotensin-converting enzyme (ACE) inhibitor, an AT-1 receptor blocking agent, a β-receptor blocking agent, and an aldosterone antagonist.

12. The method of claim 9, wherein said therapy is an interventional therapy.

13. The method of claim 12, wherein said interventional therapy is cardiac resynchronization therapy (CRT) or based on implantation of a cardioverter defibrillator (ICD).

14. A method of providing a diagnosis of at risk of a further acute cardiovascular event, for a subject suffering from a cardiovascular complication, the method comprising:
   contacting a portion of a sample from the subject with an antibody having specific binding affinity for GDF-15, thereby forming a complex between the antibody and GDF-15, the antibody having a detectable label;
   separating the complex between the antibody and GDF-15 formed in said step of contacting from antibody not comprising the complex;
   quantifying a signal from the detectable label of the antibody comprising the complex formed in said step of contacting, the signal being proportional to an amount of GDF-15 in the sample, whereby an amount of GDF-15 in the sample is calculated;
   comparing the amount of GDF-15 calculated in said step of quantifying to a reference amount for GDF-15, the reference amount for GDF-15 being 1200 pg/ml;
   contacting a portion of a sample from the subject with an antibody having specific binding affinity for a natriuretic peptide, thereby forming a complex between the antibody and natriuretic peptide, the antibody having a detectable label;
   separating the complex between the antibody and natriuretic peptide formed in said step of contacting from antibody not comprising the complex;
   comparing the amount of natriuretic peptide calculated in said step of quantifying to a reference amount for natriuretic peptide;
   contacting a portion of a sample from the subject with an antibody having specific binding affinity for a cardiac troponin, thereby forming a complex between the antibody and cardiac troponin, the antibody having a detectable label;
   separating the complex between the antibody and cardiac troponin formed in said step of contacting from antibody not comprising the complex;
   comparing the amount of cardiac troponin calculated in said step of quantifying to a reference amount for cardiac troponin; and
   providing a diagnosis of at risk of a further acute cardiovascular event if the amount of the GDF-15 calculated in said step of quantifying is greater than the GDF-15 reference amount and the amount of the natriuretic peptide calculated in said step of quantifying is greater than the natriuretic peptide reference amount and the amount of the cardiac troponin calculated in said step of quantifying is greater than the cardiac troponin reference amount.

15. The method of claim 14, wherein said cardiovascular complication is an acute coronary syndrome or heart failure.

16. The method of claim 14, wherein said natriuretic peptide is NT-proBNP.

17. The method of claim 14, wherein said cardiac troponin is troponin T.

18. The method of claim 14, wherein said reference amount of cardiac troponin is 0.01 ng/ml.

19. The method of claim 14, wherein said reference amount of natriuretic peptide is 1000 pg/ml.

20. A method of providing a diagnosis of elevated risk of mortality for a subject suffering from a cardiovascular complication, comprising:
contacting a portion of a sample from the subject with an antibody having specific binding affinity for GDF-15, thereby forming a complex between the antibody and GDF-15, the antibody having a detectable label;
separating the complex between the antibody and GDF-15 formed in said step of contacting from antibody not comprising the complex;
quantifying a signal from the detectable label of the antibody comprising the complex formed in said step of contacting, the signal being proportional to an amount of GDF-15 in the sample, whereby an amount of GDF-15 in the sample is calculated;
comparing the amount of GDF-15 calculated in said step of quantifying to a reference amount for GDF-15, the reference amount for GDF-15 being 1200 pg/ml;
contacting a portion of a sample from the subject with an antibody having specific binding affinity for a natriuretic peptide, thereby forming a complex between the antibody and natriuretic peptide, the antibody having a detectable label;
separating the complex between the antibody and natriuretic peptide formed in said step of contacting from antibody not comprising the complex;
quantifying a signal from the detectable label of the antibody comprising the complex formed in said step of contacting, the signal being proportional to an amount of natriuretic peptide in the sample, whereby an amount of natriuretic peptide in the sample is calculated;
comparing the amount of natriuretic peptide calculated in said step of quantifying to a reference amount for natriuretic peptide; and
providing a diagnosis of elevated risk of mortality if the amount of the GDF-15 calculated in said step of quantifying is greater than the GDF-15 reference amount and the amount of the natriuretic peptide calculated in said step of quantifying is greater than the natriuretic peptide reference amount.

21. The method of claim 20, wherein said cardiovascular complication is an acute coronary syndrome or heart failure.

22. The method of claim 20, wherein said natriuretic peptide is NT-proBNP.

23. The method of claim 20, wherein said reference amount of natriuretic peptide is 1000 pg/ml.

24. A method of providing a diagnosis of at risk of an adverse cardiovascular complication for a subject suffering from heart failure, comprising:
contacting a portion of a sample from the subject with an antibody having specific binding affinity for GDF-15, thereby forming a complex between the antibody and GDF-15, the antibody having a detectable label;
separating the complex between the antibody and GDF-15 formed in said step of contacting from antibody not comprising the complex;
quantifying a signal from the detectable label of the antibody comprising the complex formed in said step of contacting, the signal being proportional to an amount of GDF-15 in the sample, whereby an amount of GDF-15 in the sample is calculated;
comparing the amount of GDF-15 calculated in said step of quantifying to a reference amount for GDF-15, the reference amount for GDF-15 being 1200 pg/ml; and
providing a diagnosis of at risk of an adverse cardiovascular complication if the amount of the GDF-15 calculated in said step of quantifying is greater than the GDF-15 reference amount.

25. A method of providing a diagnosis of at risk of a subsequent pulmonary embolism-related complication for a subject suffering from pulmonary embolism, comprising:
contacting a portion of a sample from the subject with an antibody having specific binding affinity for GDF-15, thereby forming a complex between the antibody and GDF-15, the antibody having a detectable label;
separating the complex between the antibody and GDF-15 formed in said step of contacting from antibody not comprising the complex;
quantifying a signal from the detectable label of the antibody comprising the complex formed in said step of contacting, the signal being proportional to an amount of GDF-15 in the sample, whereby an amount of GDF-15 in the sample is calculated;
comparing the amount of GDF-15 calculated in said step of quantifying to a reference amount for GDF-15, wherein the reference amount defined a threshold amount of GDF-15 being 1200 pg/ml; and
providing a diagnosis of at risk of a subsequent pulmonary embolism-related complication if the amount of the GDF-15 calculated in said step of quantifying is greater than the GDF-15 reference amount.

26. The method of claim 1, wherein said steps of quantifying and comparing comprise use of a computing device executing a computer program.

27. The method of claim 26, wherein said step of identifying comprises the computing device providing an output result.

28. The method of claim 14, wherein said steps of quantifying and comparing comprise use of a computing device executing a computer program, and wherein said step of providing comprises the computing device providing an output result.

29. The method of claim 20, wherein said steps of quantifying the signal proportional to the amount of GDF-15 in the sample, comparing the amount of GDF-15 calculated in said step of quantifying, quantifying the signal proportional to the amount of natriuretic peptide in the sample, and comparing the amount of natriuretic peptide calculated in said step of quantifying comprise use of a computing device executing a computer program, and wherein said step of providing comprises the computing device providing an output result.

30. The method of claim 24, wherein said steps of quantifying and comparing comprise use of a computing device executing a computer program, and wherein said step of providing comprises the computing device providing an output result.

31. The method of claim 25, wherein said steps of quantifying and comparing comprise use of a computing device executing a computer program, and wherein said step of providing comprises the computing device providing an output result.

32. The method of claim 1 further comprising the step of
contacting the portion of the sample from the subject with a capture antibody, the capture antibody having specific binding affinity for an epitope of GDF-15 not bound by the antibody, thereby forming a complex between the capture antibody and GDF-15, the capture antibody coupled to one of streptavidin and biotin, said step of contacting the portion of the sample with the capture antibody occurring prior to said steps of separating and quantifying, wherein upon said steps of contacting the portion of the sample with the antibody and contacting the portion of the sample with the capture antibody, a complex between the antibody, GDF-15 and the capture antibody is thereby formed.

33. The method of claim 32, wherein said step of separating comprises contacting the complex between the antibody, GDF-15 and the capture antibody with a magnetic bead coupled to the other of streptavidin and biotin.

34. The method of claim 24 further comprising the step of
contacting the portion of the sample from the subject with a capture antibody, the capture antibody having specific binding affinity for an epitope of GDF-15 not bound by the antibody, thereby forming a complex between the capture antibody and GDF-15, the capture antibody coupled to one of streptavidin and biotin, said step of contacting the portion of the sample with the capture antibody occurring prior to said steps of separating and quantifying, wherein upon said steps of contacting the portion of the sample with the antibody and contacting the portion of the sample with the capture antibody, a complex between the antibody, GDF-15 and the capture antibody is thereby formed.

35. The method of claim 34, wherein said step of separating comprises contacting the complex between the antibody, GDF-15 and the capture antibody with a magnetic bead coupled to the other of streptavidin and biotin.

* * * * *